United States Patent
Strauss et al.

(10) Patent No.: US 8,801,747 B2
(45) Date of Patent: Aug. 12, 2014

(54) IMPLANT, A MANDREL, AND A METHOD OF FORMING AN IMPLANT

(75) Inventors: Brian Michael Strauss, Trabuco Canyon, CA (US); Todd Jeffrey Hewitt, Laguna Niguel, CA (US); Ramon Torres Carrillo, Santa Ana, CA (US); Khoa Dang Vu, Santa Ana, CA (US); William Robert Patterson, Irvine, CA (US); Lawrason Charles Wilbur, Lake Forest, CA (US); Justin Klotz, Placentia, CA (US); Scott William Brennan, Laguna Beach, CA (US); Vince Divino, Mission Viejo, CA (US)

(73) Assignee: Covidien LP, Mansfield, MA (US)

( * ) Notice: Subject to any disclaimer, the term of this patent is extended or adjusted under 35 U.S.C. 154(b) by 605 days.

(21) Appl. No.: 12/038,737

(22) Filed: Feb. 27, 2008

(65) Prior Publication Data

US 2008/0228216 A1 Sep. 18, 2008

Related U.S. Application Data

(60) Provisional application No. 60/894,589, filed on Mar. 13, 2007, provisional application No. 60/894,858, filed on Mar. 14, 2007, provisional application No. 60/894,865, filed on Mar. 14, 2007.

(51) Int. Cl.
*A61M 29/00* (2006.01)

(52) U.S. Cl.
USPC .......................................................... 606/200

(58) Field of Classification Search
USPC .................. 606/113, 114, 191, 194, 198, 200
See application file for complete search history.

(56) References Cited

U.S. PATENT DOCUMENTS

| | | |
|---|---|---|
| 3,334,629 A | 8/1967 | Colm |
| 3,834,394 A | 9/1974 | Hunter et al. |
| 4,085,757 A | 4/1978 | Pevsner |
| 4,282,875 A | 8/1981 | Serbinenko et al. |
| 4,311,146 A | 1/1982 | Wonder |
| 4,327,734 A | 5/1982 | White, Jr. |
| 4,341,218 A | 7/1982 | U |
| 4,346,712 A | 8/1982 | Handa et al. |
| 4,364,392 A | 12/1982 | Strother et al. |

(Continued)

FOREIGN PATENT DOCUMENTS

| | | |
|---|---|---|
| CA | 2144725 A1 | 5/1994 |
| CA | 2265062 A1 | 9/1999 |

(Continued)

OTHER PUBLICATIONS

Meriam-Webster dictionary definition for "twist".*

(Continued)

*Primary Examiner* — Ryan Severson
*Assistant Examiner* — Katherine M Shi
(74) *Attorney, Agent, or Firm* — Elizabeth A. O'Brien, Esq.

(57) ABSTRACT

This invention is directed to an implant having a coil for embolizing a vascular site, such as aneurysm. The coil has a specific three-dimensional shape that is achieved by winding the coil around a mandrel in a specific pattern and then heat setting the coil and the mandrel, another aspect of the invention. The three-dimensional shape resembles unclosed mobius loops. Also provided are methods of making the coil and methods of embolizing vascular site.

16 Claims, 10 Drawing Sheets

(56) References Cited

U.S. PATENT DOCUMENTS

| | | |
|---|---|---|
| 4,402,319 A | 9/1983 | Handa et al. |
| 4,441,495 A | 4/1984 | Hicswa |
| 4,494,531 A | 1/1985 | Gianturco |
| 4,517,979 A | 5/1985 | Pecenka |
| 4,545,367 A | 10/1985 | Tucci |
| 4,638,803 A | 1/1987 | Rand |
| 4,719,924 A | 1/1988 | Crittenden et al. |
| 4,735,201 A | 4/1988 | O'Reilly |
| 4,745,919 A | 5/1988 | Bundy et al. |
| 4,781,177 A | 11/1988 | Lebigot |
| 4,787,899 A | 11/1988 | Lazarus |
| 4,819,637 A | 4/1989 | Dormandy, Jr. et al. |
| 4,832,055 A | 5/1989 | Palestrant |
| 4,932,419 A | 6/1990 | de Toledo |
| 4,944,746 A | 7/1990 | Iwata et al. |
| 4,957,501 A | 9/1990 | Lahille et al. |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,035,706 A | 7/1991 | Giantureo et al. |
| 5,037,427 A | 8/1991 | Harada et al. |
| 5,062,829 A | 11/1991 | Pryor et al. |
| 5,104,399 A | 4/1992 | Lazarus |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,731 A | 7/1992 | Butler et al. |
| 5,133,732 A | 7/1992 | Wiktor |
| 5,147,370 A | 9/1992 | McNamara et al. |
| 5,167,624 A | 12/1992 | Butler et al. |
| 5,181,921 A | 1/1993 | Makita et al. |
| 5,192,301 A | 3/1993 | Kamiya et al. |
| 5,211,658 A | 5/1993 | Clouse |
| 5,217,484 A | 6/1993 | Marks |
| 5,222,970 A | 6/1993 | Reeves |
| 5,224,953 A | 7/1993 | Morgentaler |
| 5,226,911 A | 7/1993 | Chee et al. |
| 5,234,437 A | 8/1993 | Sepetka |
| 5,250,071 A | 10/1993 | Palermo |
| 5,256,146 A | 10/1993 | Ensminger et al. |
| 5,261,916 A | 11/1993 | Engelson |
| 5,263,964 A | 11/1993 | Purdy |
| 5,304,194 A | 4/1994 | Chee et al. |
| 5,304,195 A | 4/1994 | Twyford, Jr. et al. |
| 5,312,415 A | 5/1994 | Palermo |
| 5,314,472 A | 5/1994 | Fontaine |
| 5,334,210 A | 8/1994 | Gianturco |
| 5,350,397 A | 9/1994 | Palermo et al. |
| 5,354,295 A | 10/1994 | Guglielmi et al. |
| 5,368,592 A | 11/1994 | Stern et al. |
| 5,382,259 A | 1/1995 | Phelps et al. |
| 5,382,260 A | 1/1995 | Dormandy, Jr. et al. |
| 5,382,261 A | 1/1995 | Palmaz |
| 5,397,345 A | 3/1995 | Lazarus |
| 5,417,708 A | 5/1995 | Hall et al. |
| 5,423,829 A | 6/1995 | Pham et al. |
| 5,423,849 A | 6/1995 | Engelson et al. |
| 5,443,454 A | 8/1995 | Tanabe et al. |
| 5,443,478 A | 8/1995 | Purdy |
| 5,456,693 A | 10/1995 | Conston et al. |
| 5,476,472 A | 12/1995 | Dormandy, Jr. et al. |
| 5,480,382 A | 1/1996 | Hammerslag et al. |
| 5,498,227 A | 3/1996 | Mawad |
| 5,507,769 A | 4/1996 | Marin et al. |
| 5,522,822 A | 6/1996 | Phelps et al. |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,549,624 A | 8/1996 | Mirigian et al. |
| 5,556,426 A | 9/1996 | Popadiuk et al. |
| 5,562,698 A | 10/1996 | Parker |
| 5,569,245 A | 10/1996 | Guglielmi et al. |
| 5,573,520 A | 11/1996 | Schwartz et al. |
| 5,578,074 A | 11/1996 | Mirigian |
| 5,582,619 A | 12/1996 | Ken |
| 5,601,600 A | 2/1997 | Ton |
| 5,624,449 A | 4/1997 | Pham et al. |
| 5,624,461 A | 4/1997 | Mariant |
| 5,626,599 A | 5/1997 | Bourne et al. |
| 5,634,928 A | 6/1997 | Fischell et al. |
| 5,639,277 A | 6/1997 | Mariant et al. |
| 5,643,254 A | 7/1997 | Scheldrup et al. |
| 5,645,558 A | 7/1997 | Horton |
| 5,645,564 A | 7/1997 | Northrup et al. |
| 5,649,949 A | 7/1997 | Wallace et al. |
| 5,658,308 A | 8/1997 | Snyder |
| 5,662,700 A | 9/1997 | Lazarus |
| 5,669,905 A | 9/1997 | Scheldrup et al. |
| 5,669,931 A | 9/1997 | Kupiecki et al. |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,695,517 A | 12/1997 | Marin et al. |
| 5,700,258 A | 12/1997 | Mirigian et al. |
| 5,702,361 A | 12/1997 | Evans et al. |
| 5,718,711 A | 2/1998 | Berenstein et al. |
| 5,725,534 A | 3/1998 | Rasmussen |
| 5,725,546 A | 3/1998 | Samson |
| 5,725,552 A | 3/1998 | Kotula et al. |
| 5,733,329 A | 3/1998 | Wallace et al. |
| 5,743,905 A | 4/1998 | Eder et al. |
| 5,746,734 A | 5/1998 | Dormandy, Jr. et al. |
| 5,746,769 A | 5/1998 | Ton et al. |
| 5,749,891 A | 5/1998 | Ken et al. |
| 5,749,894 A | 5/1998 | Engelson |
| 5,749,918 A | 5/1998 | Hogendijk et al. |
| 5,759,161 A | 6/1998 | Ogawa et al. |
| 5,766,219 A | 6/1998 | Horton |
| 5,797,953 A | 8/1998 | Tekulve |
| 5,800,426 A | 9/1998 | Taki et al. |
| 5,800,453 A | 9/1998 | Gia |
| 5,800,455 A | 9/1998 | Palermo et al. |
| 5,814,062 A | 9/1998 | Sepetka et al. |
| 5,830,230 A | 11/1998 | Berryman et al. |
| 5,833,705 A | 11/1998 | Ken et al. |
| 5,843,118 A | 12/1998 | Sepetka et al. |
| 5,846,210 A | 12/1998 | Ogawa et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,058 A | 4/1999 | Taki et al. |
| 5,891,128 A | 4/1999 | Gia et al. |
| 5,891,130 A | 4/1999 | Palermo et al. |
| 5,891,155 A | 4/1999 | Irie |
| 5,891,192 A | 4/1999 | Murayama et al. |
| 5,895,385 A | 4/1999 | Guglielmi et al. |
| 5,895,391 A | 4/1999 | Farnholtz |
| 5,895,410 A | 4/1999 | Forber et al. |
| 5,895,411 A | 4/1999 | Irie |
| 5,911,731 A | 6/1999 | Pham et al. |
| 5,911,737 A | 6/1999 | Lee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |
| 5,925,060 A | 7/1999 | Forber |
| 5,925,062 A | 7/1999 | Purdy |
| 5,928,226 A | 7/1999 | Guglielmi et al. |
| 5,935,145 A | 8/1999 | Villar et al. |
| 5,935,148 A | 8/1999 | Villar et al. |
| 5,941,249 A | 8/1999 | Maynard |
| 5,941,888 A | 8/1999 | Wallace et al. |
| 5,944,714 A | 8/1999 | Guglielmi et al. |
| 5,944,733 A | 8/1999 | Engelson |
| 5,947,962 A | 9/1999 | Guglielmi et al. |
| 5,947,963 A | 9/1999 | Guglielmi |
| 5,957,948 A | 9/1999 | Mariant |
| 5,964,797 A | 10/1999 | Ho |
| 5,972,019 A | 10/1999 | Engelson et al. |
| 5,976,126 A | 11/1999 | Guglielmi |
| 5,976,131 A | 11/1999 | Guglielmi et al. |

(56) References Cited

U.S. PATENT DOCUMENTS

| | | | |
|---|---|---|---|
| 5,976,152 A | 11/1999 | Regan et al. | |
| 5,976,162 A | 11/1999 | Doan et al. | |
| 5,980,514 A | 11/1999 | Kupiecki et al. | |
| 5,980,550 A | 11/1999 | Eder et al. | |
| 5,980,554 A | 11/1999 | Lenker et al. | |
| 5,984,929 A | 11/1999 | Bashiri et al. | |
| 5,984,944 A | 11/1999 | Forber | |
| 5,989,242 A | 11/1999 | Saadat et al. | |
| 6,001,092 A | 12/1999 | Mirigian et al. | |
| 6,004,338 A | 12/1999 | Ken et al. | |
| 6,010,498 A | 1/2000 | Guglielmi | |
| 6,013,084 A | 1/2000 | Ken et al. | |
| 6,015,424 A | 1/2000 | Rosenbluth et al. | |
| 6,017,364 A | 1/2000 | Lazarus | |
| 6,017,977 A | 1/2000 | Evans et al. | |
| 6,019,757 A | 2/2000 | Scheldrup | |
| 6,019,779 A | 2/2000 | Thorud et al. | |
| 6,022,369 A | 2/2000 | Jacobsen et al. | |
| 6,024,754 A | 2/2000 | Engelson | |
| 6,024,765 A | 2/2000 | Wallace et al. | |
| 6,030,413 A | 2/2000 | Lazarus | |
| 6,033,423 A | 3/2000 | Ken et al. | |
| 6,039,749 A | 3/2000 | Marin et al. | |
| 6,056,770 A | 5/2000 | Epstein et al. | |
| 6,059,779 A | 5/2000 | Mills | |
| 6,059,815 A | 5/2000 | Lee et al. | |
| 6,063,070 A | 5/2000 | Eder | |
| 6,063,100 A | 5/2000 | Diaz et al. | |
| 6,063,104 A | 5/2000 | Villar et al. | |
| 6,066,133 A | 5/2000 | Guglielmi et al. | |
| 6,066,149 A | 5/2000 | Samson et al. | |
| 6,068,644 A | 5/2000 | Lulo et al. | |
| 6,074,407 A | 6/2000 | Levine et al. | |
| 6,077,260 A | 6/2000 | Wheelock et al. | |
| D427,680 S | 7/2000 | Mariant et al. | |
| 6,083,220 A | 7/2000 | Guglielmi et al. | |
| 6,086,577 A | 7/2000 | Ken et al. | |
| 6,090,125 A | 7/2000 | Horton | |
| 6,093,199 A | 7/2000 | Brown et al. | |
| 6,096,034 A | 8/2000 | Kupiecki et al. | |
| 6,099,546 A | 8/2000 | Gia | |
| 6,102,917 A | 8/2000 | Maitland et al. | |
| 6,102,932 A | 8/2000 | Kurz | |
| 6,102,933 A | 8/2000 | Lee et al. | |
| 6,113,622 A | 9/2000 | Hieshima | |
| 6,117,142 A | 9/2000 | Goodson et al. | |
| 6,117,157 A | 9/2000 | Tekulve | |
| 6,123,714 A | 9/2000 | Gia et al. | |
| 6,126,672 A | 10/2000 | Berryman et al. | |
| 6,136,015 A * | 10/2000 | Kurz et al. | 606/191 |
| 6,143,007 A | 11/2000 | Mariant et al. | |
| 6,146,373 A | 11/2000 | Cragg et al. | |
| 6,149,664 A | 11/2000 | Kurz | |
| 6,149,681 A | 11/2000 | Houser et al. | |
| 6,156,061 A | 12/2000 | Wallace et al. | |
| 6,159,165 A | 12/2000 | Ferrera et al. | |
| 6,159,206 A | 12/2000 | Ogawa | |
| 6,165,178 A | 12/2000 | Bashiri et al. | |
| 6,165,193 A | 12/2000 | Greene, Jr. et al. | |
| 6,165,198 A | 12/2000 | McGurk et al. | |
| 6,168,570 B1 | 1/2001 | Ferrera | |
| 6,168,592 B1 | 1/2001 | Kupiecki et al. | |
| 6,168,610 B1 | 1/2001 | Marin et al. | |
| 6,168,615 B1 | 1/2001 | Ken et al. | |
| 6,168,622 B1 | 1/2001 | Mazzocchi | |
| 6,171,326 B1 | 1/2001 | Ferrera et al. | |
| 6,183,491 B1 | 2/2001 | Lulo | |
| 6,183,495 B1 | 2/2001 | Lenker et al. | |
| 6,187,024 B1 | 2/2001 | Boock et al. | |
| 6,187,027 B1 | 2/2001 | Mariant et al. | |
| 6,190,373 B1 | 2/2001 | Palermo et al. | |
| 6,193,708 B1 | 2/2001 | Ken et al. | |
| 6,193,728 B1 | 2/2001 | Ken et al. | |
| RE37,117 E | 3/2001 | Palermo | |
| 6,202,261 B1 | 3/2001 | Moore et al. | |
| 6,203,547 B1 | 3/2001 | Nguyen et al. | |
| 6,221,066 B1 | 4/2001 | Ferrera et al. | |
| 6,221,086 B1 | 4/2001 | Forber | |
| 6,224,610 B1 | 5/2001 | Ferrera | |
| 6,231,573 B1 | 5/2001 | Amor et al. | |
| 6,231,586 B1 | 5/2001 | Mariant | |
| 6,231,590 B1 | 5/2001 | Slaikeu et al. | |
| 6,231,597 B1 | 5/2001 | Deem et al. | |
| 6,238,403 B1 | 5/2001 | Greene, Jr. et al. | |
| 6,238,415 B1 | 5/2001 | Sepetka et al. | |
| 6,241,691 B1 | 6/2001 | Ferrera et al. | |
| 6,254,592 B1 | 7/2001 | Samson et al. | |
| 6,270,495 B1 | 8/2001 | Palermo | |
| 6,277,125 B1 | 8/2001 | Barry et al. | |
| 6,277,126 B1 | 8/2001 | Barry et al. | |
| 6,280,457 B1 | 8/2001 | Wallace et al. | |
| 6,281,263 B1 | 8/2001 | Evans et al. | |
| 6,287,315 B1 | 9/2001 | Wijeratne et al. | |
| 6,287,318 B1 | 9/2001 | Villar et al. | |
| 6,293,960 B1 | 9/2001 | Ken | |
| 6,296,622 B1 | 10/2001 | Kurz et al. | |
| 6,299,619 B1 | 10/2001 | Greene, Jr. et al. | |
| 6,299,627 B1 | 10/2001 | Eder et al. | |
| 6,306,153 B1 | 10/2001 | Kurz et al. | |
| 6,312,405 B1 | 11/2001 | Meyer et al. | |
| 6,312,421 B1 | 11/2001 | Boock | |
| 6,315,709 B1 | 11/2001 | Garibaldi et al. | |
| 6,319,267 B1 | 11/2001 | Kurz | |
| 6,322,576 B1 | 11/2001 | Wallace et al. | |
| 6,328,750 B1 | 12/2001 | Berry et al. | |
| 6,331,184 B1 | 12/2001 | Abrams | |
| 6,335,384 B1 | 1/2002 | Evans et al. | |
| 6,344,041 B1 | 2/2002 | Kupiecki et al. | |
| 6,344,048 B1 | 2/2002 | Chin et al. | |
| 6,346,091 B1 | 2/2002 | Jacobsen et al. | |
| 6,346,117 B1 | 2/2002 | Greenhalgh | |
| 6,348,041 B1 | 2/2002 | Klint | |
| 6,361,547 B1 | 3/2002 | Hieshima | |
| 6,364,823 B1 | 4/2002 | Garibaldi et al. | |
| 6,368,338 B1 | 4/2002 | Konya et al. | |
| 6,371,972 B1 | 4/2002 | Wallace et al. | |
| 6,375,606 B1 | 4/2002 | Garibaldi et al. | |
| 6,375,628 B1 | 4/2002 | Zadno-Azizi et al. | |
| 6,375,668 B1 | 4/2002 | Gifford et al. | |
| 6,375,669 B1 | 4/2002 | Rosenbluth et al. | |
| 6,379,329 B1 | 4/2002 | Naglreiter et al. | |
| 6,379,374 B1 | 4/2002 | Hieshima et al. | |
| 6,383,146 B1 | 5/2002 | Klint | |
| 6,383,174 B1 | 5/2002 | Eder | |
| 6,383,204 B1 | 5/2002 | Ferrera et al. | |
| 6,383,205 B1 | 5/2002 | Samson et al. | |
| 6,409,721 B1 | 6/2002 | Wheelock et al. | |
| 6,416,535 B1 | 7/2002 | Lazarus | |
| 6,416,541 B2 | 7/2002 | Denardo | |
| 6,423,085 B1 | 7/2002 | Murayama et al. | |
| 6,425,893 B1 | 7/2002 | Guglielmi | |
| 6,425,914 B1 | 7/2002 | Wallace et al. | |
| 6,428,557 B1 | 8/2002 | Hilaire | |
| 6,428,558 B1 | 8/2002 | Jones et al. | |
| 6,454,780 B1 | 9/2002 | Wallace | |
| 6,458,119 B1 | 10/2002 | Berenstein et al. | |
| 6,458,127 B1 | 10/2002 | Truckai et al. | |
| 6,458,137 B1 | 10/2002 | Klint | |
| 6,464,699 B1 | 10/2002 | Swanson | |
| 6,468,266 B1 | 10/2002 | Bashiri et al. | |
| 6,475,169 B2 | 11/2002 | Ferrera | |
| 6,475,227 B2 | 11/2002 | Burke et al. | |
| 6,478,773 B1 | 11/2002 | Gandhi et al. | |
| 6,485,524 B2 | 11/2002 | Strecker | |
| 6,494,884 B2 | 12/2002 | Gifford, III et al. | |
| 6,500,149 B2 | 12/2002 | Gandhi et al. | |
| 6,500,190 B2 | 12/2002 | Greene, Jr. et al. | |
| 6,506,204 B2 | 1/2003 | Mazzocchi | |
| 6,511,468 B1 | 1/2003 | Cragg et al. | |
| 6,514,264 B1 | 2/2003 | Naglreiter | |
| 6,530,934 B1 | 3/2003 | Jacobsen et al. | |
| 6,533,801 B2 | 3/2003 | Wallace et al. | |
| 6,537,293 B1 | 3/2003 | Berryman et al. | |
| 6,540,657 B2 | 4/2003 | Cross, III et al. | |

(56) References Cited

U.S. PATENT DOCUMENTS

| | | |
|---|---|---|
| 6,544,163 B2 | 4/2003 | Wallace et al. |
| 6,544,225 B1 | 4/2003 | Lulo et al. |
| 6,544,268 B1 | 4/2003 | Lazarus |
| 6,544,275 B1 | 4/2003 | Teoh |
| 6,547,804 B2 | 4/2003 | Porter et al. |
| 6,551,305 B2 | 4/2003 | Ferrera et al. |
| 6,551,340 B1 | 4/2003 | Konya et al. |
| 6,554,849 B1 | 4/2003 | Jones et al. |
| 6,558,367 B1 | 5/2003 | Cragg et al. |
| 6,569,179 B2 | 5/2003 | Teoh et al. |
| 6,572,628 B2 | 6/2003 | Dominguez et al. |
| 6,575,994 B1 | 6/2003 | Marin et al. |
| 6,585,748 B1 | 7/2003 | Jeffree |
| 6,585,754 B2 | 7/2003 | Wallace et al. |
| 6,589,227 B2 | 7/2003 | Sønderskov Klint |
| 6,589,230 B2 | 7/2003 | Gia et al. |
| 6,589,236 B2 | 7/2003 | Wheelock et al. |
| 6,589,265 B1 | 7/2003 | Palmer et al. |
| 6,592,605 B2 | 7/2003 | Lenker et al. |
| 6,602,261 B2 | 8/2003 | Greene et al. |
| 6,602,269 B2 | 8/2003 | Wallace et al. |
| 6,603,994 B2 | 8/2003 | Wallace et al. |
| 6,605,101 B1 | 8/2003 | Schaefer et al. |
| 6,607,538 B1 | 8/2003 | Ferrera et al. |
| 6,607,539 B1 | 8/2003 | Hayashi et al. |
| 6,610,085 B1 | 8/2003 | Lazarus |
| 6,613,074 B1 | 9/2003 | Mitelberg et al. |
| 6,616,617 B1 | 9/2003 | Ferrera et al. |
| 6,620,152 B2 | 9/2003 | Guglielmi |
| 6,623,493 B2 | 9/2003 | Wallace et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,638,291 B1 | 10/2003 | Ferrera et al. |
| 6,638,293 B1 | 10/2003 | Makower et al. |
| 6,656,173 B1 | 12/2003 | Palermo |
| 6,656,201 B2 | 12/2003 | Ferrera et al. |
| 6,656,218 B1 | 12/2003 | Denardo et al. |
| 6,656,351 B2 | 12/2003 | Boyle |
| 6,660,020 B2 | 12/2003 | Wallace et al. |
| 6,663,607 B2 | 12/2003 | Slaikeu et al. |
| 6,679,903 B2 | 1/2004 | Kurz |
| 6,685,653 B2 | 2/2004 | Ehr et al. |
| 6,685,696 B2 | 2/2004 | Fleischhacker et al. |
| 6,689,141 B2 | 2/2004 | Ferrera et al. |
| 6,692,510 B2 | 2/2004 | West |
| 6,702,844 B1 | 3/2004 | Lazarus |
| 6,716,238 B2 | 4/2004 | Elliott |
| 6,723,112 B2 | 4/2004 | Ho et al. |
| 6,743,236 B2 | 6/2004 | Barry et al. |
| 6,743,251 B1 | 6/2004 | Eder |
| 6,767,358 B2 | 7/2004 | Leonhardt et al. |
| 6,811,561 B2 | 11/2004 | Diaz et al. |
| 6,814,748 B1 | 11/2004 | Baker et al. |
| 6,835,185 B2 | 12/2004 | Ramzipoor et al. |
| 6,849,081 B2 | 2/2005 | Sepetka et al. |
| 6,852,116 B2 | 2/2005 | Leonhardt et al. |
| 6,853,418 B2 | 2/2005 | Suzuki et al. |
| 6,855,153 B2 | 2/2005 | Saadat |
| 6,855,155 B2 | 2/2005 | Denardo et al. |
| 6,860,893 B2 | 3/2005 | Wallace et al. |
| 6,860,901 B1 | 3/2005 | Baker et al. |
| 6,872,218 B2 | 3/2005 | Ferrera et al. |
| 6,878,163 B2 | 4/2005 | Denardo et al. |
| 6,905,503 B2 | 6/2005 | Gifford, III et al. |
| 6,913,618 B2 | 7/2005 | Denardo et al. |
| 6,929,654 B2 | 8/2005 | Teoh et al. |
| 6,945,956 B2 | 9/2005 | Waldhauser et al. |
| 6,958,061 B2 | 10/2005 | Truckai et al. |
| 6,958,068 B2 | 10/2005 | Hieshima |
| 6,964,657 B2 | 11/2005 | Cragg et al. |
| 6,966,892 B2 | 11/2005 | Gandhi et al. |
| 6,984,240 B1 | 1/2006 | Ken et al. |
| 6,994,711 B2 | 2/2006 | Hieshima et al. |
| 7,014,645 B2 | 3/2006 | Greene, Jr. et al. |
| 7,029,486 B2 | 4/2006 | Schaefer et al. |
| 7,029,487 B2 | 4/2006 | Greene, Jr. et al. |
| 7,033,374 B2 | 4/2006 | Schaefer et al. |
| 7,058,456 B2 | 6/2006 | Pierce |
| 7,060,083 B2 | 6/2006 | Gerberding |
| 7,070,607 B2 | 7/2006 | Murayama et al. |
| 7,147,618 B2 | 12/2006 | Kurz |
| 7,169,161 B2 | 1/2007 | Bonnette et al. |
| 7,182,774 B2 | 2/2007 | Barry et al. |
| 7,198,613 B2 | 4/2007 | Gandhi et al. |
| 7,238,194 B2 | 7/2007 | Monstadt et al. |
| 7,300,458 B2 | 11/2007 | Henkes et al. |
| 7,316,701 B2 | 1/2008 | Ferrera et al. |
| 7,323,000 B2 | 1/2008 | Monstadt et al. |
| 7,331,973 B2 | 2/2008 | Gesswein et al. |
| 7,344,558 B2 | 3/2008 | Lorenzo et al. |
| 7,410,482 B2 | 8/2008 | Murphy et al. |
| 7,473,266 B2 | 1/2009 | Glaser |
| 7,485,122 B2 | 2/2009 | Teoh |
| 7,485,317 B1 | 2/2009 | Murayama et al. |
| 7,524,322 B2 | 4/2009 | Monstadt et al. |
| 7,575,582 B2 | 8/2009 | Gandhi et al. |
| 7,578,826 B2 | 8/2009 | Gandhi et al. |
| RE41,029 E | 12/2009 | Guglielmi et al. |
| 7,691,124 B2 | 4/2010 | Balgobin |
| 7,708,755 B2 | 5/2010 | Davis, III et al. |
| 7,722,636 B2 | 5/2010 | Farnan |
| 7,722,637 B2 | 5/2010 | Barry et al. |
| 7,766,933 B2 | 8/2010 | Davis, III et al. |
| 7,811,305 B2 | 10/2010 | Balgobin et al. |
| 7,841,994 B2 | 11/2010 | Skujins et al. |
| 7,879,064 B2 | 2/2011 | Monstadt et al. |
| 7,883,526 B2 | 2/2011 | Jones et al. |
| 7,896,899 B2 | 3/2011 | Patterson et al. |
| 7,901,444 B2 | 3/2011 | Slazas |
| 7,901,704 B2 | 3/2011 | Richard |
| 7,918,872 B2 | 4/2011 | Mitelberg et al. |
| 7,938,845 B2 | 5/2011 | Aganon et al. |
| 7,955,272 B2 | 6/2011 | Rooney et al. |
| 8,002,789 B2 | 8/2011 | Ramzipoor et al. |
| 8,007,509 B2 | 8/2011 | Buiser et al. |
| 8,372,110 B2 | 2/2013 | Monstadt et al. |
| 2002/0010481 A1* | 1/2002 | Jayaraman ................ 606/151 |
| 2002/0019647 A1 | 2/2002 | Wallace et al. |
| 2002/0065529 A1 | 5/2002 | Laurent et al. |
| 2002/0072712 A1 | 6/2002 | Nool et al. |
| 2002/0072791 A1 | 6/2002 | Eder et al. |
| 2002/0082620 A1 | 6/2002 | Lee |
| 2002/0087184 A1 | 7/2002 | Eder et al. |
| 2002/0120297 A1 | 8/2002 | Shadduck |
| 2002/0128671 A1 | 9/2002 | Wallace et al. |
| 2002/0138095 A1 | 9/2002 | Mazzocchi et al. |
| 2002/0143349 A1 | 10/2002 | Gifford, III et al. |
| 2002/0169473 A1 | 11/2002 | Sepetka et al. |
| 2003/0014073 A1 | 1/2003 | Bashiri et al. |
| 2003/0040733 A1 | 2/2003 | Cragg et al. |
| 2003/0045901 A1 | 3/2003 | Opolski |
| 2003/0083676 A1 | 5/2003 | Wallace |
| 2003/0130689 A1 | 7/2003 | Wallace et al. |
| 2003/0169473 A1 | 9/2003 | Cotter et al. |
| 2003/0176857 A1 | 9/2003 | Lee |
| 2003/0181927 A1 | 9/2003 | Wallace |
| 2003/0216772 A1 | 11/2003 | Konya et al. |
| 2003/0225365 A1 | 12/2003 | Greff et al. |
| 2004/0002731 A1 | 1/2004 | Aganon et al. |
| 2004/0002732 A1 | 1/2004 | Teoh et al. |
| 2004/0002733 A1 | 1/2004 | Teoh |
| 2004/0006362 A1 | 1/2004 | Schaefer et al. |
| 2004/0006363 A1 | 1/2004 | Schaefer |
| 2004/0024394 A1 | 2/2004 | Wallace et al. |
| 2004/0034363 A1 | 2/2004 | Wilson et al. |
| 2004/0034378 A1 | 2/2004 | Monstadt et al. |
| 2004/0045554 A1 | 3/2004 | Schaefer et al. |
| 2004/0078050 A1 | 4/2004 | Monstadt et al. |
| 2004/0106946 A1 | 6/2004 | Ferrera et al. |
| 2004/0181256 A1 | 9/2004 | Glaser |
| 2004/0193178 A1 | 9/2004 | Nikolchev |
| 2004/0193206 A1 | 9/2004 | Gerberding et al. |
| 2004/0220563 A1 | 11/2004 | Eder |

(56) References Cited

U.S. PATENT DOCUMENTS

| | | |
|---|---|---|
| 2004/0220585 A1 | 11/2004 | Nikolchev |
| 2004/0225279 A1 | 11/2004 | Raymond |
| 2004/0236344 A1 | 11/2004 | Monstadt et al. |
| 2004/0260384 A1 | 12/2004 | Allen |
| 2005/0021023 A1 | 1/2005 | Guglielmi et al. |
| 2005/0021074 A1 | 1/2005 | Elliott |
| 2005/0079196 A1 | 4/2005 | Henkes et al. |
| 2005/0171572 A1 | 8/2005 | Martinez |
| 2005/0177185 A1 | 8/2005 | Becker et al. |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1 | 4/2006 | Desai et al. |
| 2006/0106417 A1 | 5/2006 | Tessmer et al. |
| 2006/0116711 A1 | 6/2006 | Elliott et al. |
| 2006/0116714 A1 | 6/2006 | Sepetka et al. |
| 2006/0200190 A1 | 9/2006 | Lorenzo et al. |
| 2006/0271097 A1 | 11/2006 | Ramzipoor et al. |
| 2006/0276824 A1 | 12/2006 | Mitelberg |
| 2007/0055302 A1 | 3/2007 | Henry et al. |
| 2007/0083226 A1 | 4/2007 | Buiser et al. |
| 2007/0142893 A1 | 6/2007 | Buiser et al. |
| 2007/0150045 A1 | 6/2007 | Ferrera |
| 2007/0173757 A1 | 7/2007 | Levine et al. |
| 2007/0185524 A1 | 8/2007 | Diaz et al. |
| 2007/0225738 A1 | 9/2007 | Pal |
| 2007/0239193 A1 | 10/2007 | Simon et al. |
| 2007/0239199 A1 | 10/2007 | Jayaraman |
| 2007/0282425 A1 | 12/2007 | Kleine et al. |
| 2007/0299461 A1 | 12/2007 | Elliott |
| 2008/0045922 A1 | 2/2008 | Cragg et al. |
| 2008/0046092 A1 | 2/2008 | Davis et al. |
| 2008/0046093 A1 | 2/2008 | Davis et al. |
| 2008/0051803 A1 | 2/2008 | Monstadt et al. |
| 2008/0097462 A1 | 4/2008 | Mitelberg et al. |
| 2008/0103585 A1 | 5/2008 | Monstadt et al. |
| 2008/0125855 A1 | 5/2008 | Henkes et al. |
| 2008/0228215 A1 | 9/2008 | Strauss et al. |
| 2008/0300616 A1 | 12/2008 | Que et al. |
| 2008/0306504 A1 | 12/2008 | Win et al. |
| 2008/0319532 A1 | 12/2008 | Monstadt et al. |
| 2009/0069836 A1 | 3/2009 | Labdag et al. |
| 2009/0149864 A1 | 6/2009 | Porter |
| 2009/0182268 A1 | 7/2009 | Thielen et al. |
| 2009/0254111 A1 | 10/2009 | Monstadt et al. |
| 2009/0254169 A1 | 10/2009 | Spenser et al. |
| 2009/0270877 A1 | 10/2009 | Johnson et al. |
| 2009/0312748 A1 | 12/2009 | Johnson et al. |
| 2010/0004673 A1 | 1/2010 | Denison et al. |
| 2010/0004675 A1 | 1/2010 | Wilson et al. |
| 2010/0023105 A1 | 1/2010 | Levy et al. |
| 2010/0030200 A1 | 2/2010 | Strauss et al. |
| 2010/0030319 A1 | 2/2010 | Weber |
| 2010/0049165 A1 | 2/2010 | Sutherland et al. |
| 2010/0076479 A1 | 3/2010 | Monstadt |
| 2010/0174269 A1 | 7/2010 | Tompkins et al. |
| 2011/0022003 A1 | 1/2011 | Tekulve |
| 2011/0098814 A1 | 4/2011 | Monstadt et al. |
| 2011/0118777 A1 | 5/2011 | Patterson et al. |
| 2011/0172700 A1 | 7/2011 | Bose et al. |
| 2011/0184454 A1 | 7/2011 | Barry et al. |
| 2011/0213406 A1 | 9/2011 | Aganon et al. |
| 2011/0313447 A1 | 12/2011 | Strauss |
| 2012/0041470 A1 | 2/2012 | Shrivastava et al. |
| 2012/0065720 A1 | 3/2012 | Strauss et al. |
| 2012/0226305 A1 | 9/2012 | Strauss et al. |
| 2012/0313447 A1 | 12/2012 | Park et al. |
| 2013/0190801 A1 | 7/2013 | Divino et al. |
| 2013/0253572 A1 | 9/2013 | Molaei et al. |

FOREIGN PATENT DOCUMENTS

| | | |
|---|---|---|
| CN | 1668250 A | 9/2005 |
| DE | 4445715 A1 | 6/1996 |
| DE | 69627243 T2 | 1/1997 |
| DE | 195 47 617 | 9/1997 |
| DE | 19607451 A1 | 9/1997 |
| DE | 19610333 A1 | 9/1997 |
| DE | 19647280 A1 | 10/1997 |
| DE | 19952387 A1 | 5/2001 |
| DE | 10010840 A1 | 9/2001 |
| DE | 10118017 A1 | 10/2002 |
| DE | 10155191 A1 | 5/2003 |
| EP | 707830 B1 | 4/1996 |
| EP | 711532 B1 | 5/1996 |
| EP | 717969 A2 | 6/1996 |
| EP | 720838 B1 | 7/1996 |
| EP | 765636 A3 | 7/1997 |
| EP | 792623 A1 | 9/1997 |
| EP | 820726 B1 | 1/1998 |
| EP | 829236 A1 | 3/1998 |
| EP | 830873 B1 | 3/1998 |
| EP | 0 832 607 | 4/1998 |
| EP | 832607 A1 | 4/1998 |
| EP | 0 853 955 | 7/1998 |
| EP | 865773 B1 | 9/1998 |
| EP | 882428 A2 | 9/1998 |
| EP | 904737 A1 | 3/1999 |
| EP | 941700 B1 | 9/1999 |
| EP | 941701 B1 | 9/1999 |
| EP | 914807 B1 | 12/1999 |
| EP | 992220 B1 | 4/2000 |
| EP | 996372 B1 | 5/2000 |
| EP | 1005837 B1 | 6/2000 |
| EP | 1120088 A1 | 8/2001 |
| EP | 1125553 B1 | 8/2001 |
| EP | 1129666 B1 | 9/2001 |
| EP | 1142535 A2 | 10/2001 |
| EP | 1169969 A1 | 1/2002 |
| EP | 1188413 B1 | 3/2002 |
| EP | 1188414 B1 | 3/2002 |
| EP | 1295563 A1 | 3/2003 |
| EP | 1312312 B1 | 5/2003 |
| EP | 1316293 B1 | 6/2003 |
| EP | 1358850 A2 | 11/2003 |
| EP | 1374801 A1 | 1/2004 |
| EP | 1 487 526 A1 | 12/2004 |
| EP | 1 669 032 | 6/2006 |
| EP | 1 738 698 A2 | 1/2007 |
| EP | 2292147 A1 | 3/2011 |
| JP | 6-246004 A2 | 9/1994 |
| JP | 7-155331 A2 | 6/1995 |
| JP | 7-265431 A2 | 10/1995 |
| JP | 7-284534 A2 | 10/1995 |
| JP | 9-168541 A | 6/1997 |
| JP | 10-127646 A2 | 5/1998 |
| JP | 10-201766 A | 8/1998 |
| JP | 11-47138 A2 | 2/1999 |
| JP | 11-76249 A2 | 3/1999 |
| JP | 2001-513389 A | 9/2001 |
| JP | 2002-523172 A | 7/2002 |
| JP | 2004-500929 A | 1/2004 |
| JP | 2006-051349 A | 2/2006 |
| JP | 2008-525113 A | 7/2008 |
| KR | 2010107255 | 10/2010 |
| KR | 10-1014547 | 2/2011 |
| WO | WO 88/03817 | 6/1988 |
| WO | WO 89/06984 | 8/1989 |
| WO | WO 90/12616 | 11/1990 |
| WO | WO 91/13592 | 9/1991 |
| WO | WO 92/14408 | 9/1992 |
| WO | WO 92/21400 | 12/1992 |
| WO | WO 93/11719 | 6/1993 |
| WO | WO 93/16650 | 9/1993 |
| WO | WO 94/06502 | 3/1994 |
| WO | WO 94/06503 | 3/1994 |
| WO | WO 94/10936 | 5/1994 |
| WO | WO 94/11051 | 5/1994 |
| WO | WO 94/26175 | 11/1994 |
| WO | WO 95/12367 | 5/1995 |
| WO | WO 96/18343 | 6/1996 |
| WO | WO 96/32153 | 10/1996 |
| WO | WO 96/39950 | 12/1996 |

(56) References Cited

FOREIGN PATENT DOCUMENTS

| | | |
|---|---|---|
| WO | WO 97/27888 | 8/1997 |
| WO | WO 97/42881 | 11/1997 |
| WO | WO 98/09570 | 3/1998 |
| WO | WO 98/17183 | 4/1998 |
| WO | WO 98/33452 | 8/1998 |
| WO | WO-98/34546 A1 | 8/1998 |
| WO | WO 98/39048 | 9/1998 |
| WO | WO 98/58590 | 12/1998 |
| WO | WO 99/02094 | 1/1999 |
| WO | WO 99/05977 | 2/1999 |
| WO | WO 99/07292 | 2/1999 |
| WO | WO 99/09893 | 3/1999 |
| WO | WO-99/09893 | 3/1999 |
| WO | WO 99/32037 | 7/1999 |
| WO | WO 99/42038 | 8/1999 |
| WO | WO 99/44538 | 9/1999 |
| WO | WO-9949812 A2 | 10/1999 |
| WO | WO 99/56636 | 11/1999 |
| WO | WO 00/12016 | 3/2000 |
| WO | WO 00/13593 | 3/2000 |
| WO | WO 00/25680 | 5/2000 |
| WO | WO 00/44306 | 8/2000 |
| WO | WO 00/72781 | 12/2000 |
| WO | WO 01/32085 | 5/2001 |
| WO | WO 01/56500 | 8/2001 |
| WO | WO 01/58365 | 8/2001 |
| WO | WO-01/58382 A2 | 8/2001 |
| WO | WO 01/87184 | 11/2001 |
| WO | WO-01/93937 | 12/2001 |
| WO | WO 01/93937 | 12/2001 |
| WO | WO 02/02018 | 1/2002 |
| WO | WO 02/13705 | 2/2002 |
| WO | WO 02/13706 | 2/2002 |
| WO | WO 02/32496 | 4/2002 |
| WO | WO 02/39911 | 5/2002 |
| WO | WO 02/41753 | 5/2002 |
| WO | WO 02/45596 | 6/2002 |
| WO | WO 02/054943 | 7/2002 |
| WO | WO 02/054980 | 7/2002 |
| WO | WO 02/072168 | 9/2002 |
| WO | WO 02/087449 | 11/2002 |
| WO | WO 02/087651 | 11/2002 |
| WO | WO 02/089676 | 11/2002 |
| WO | WO 02/096273 | 12/2002 |
| WO | WO 02/096301 | 12/2002 |
| WO | WO 03/001970 | 1/2003 |
| WO | WO 03/007823 | 1/2003 |
| WO | WO 03/017852 | 3/2003 |
| WO | WO 03/034927 | 5/2003 |
| WO | WO 03/039624 | 5/2003 |
| WO | WO 03/041615 | 5/2003 |
| WO | WO 03/053257 | 7/2003 |
| WO | WO 03/053281 | 7/2003 |
| WO | WO 03/073914 | 9/2003 |
| WO | WO 03/077776 | 9/2003 |
| WO | WO 03/077984 | 9/2003 |
| WO | WO 03/082128 | 10/2003 |
| WO | WO 03/086240 | 10/2003 |
| WO | WO 03/092547 | 11/2003 |
| WO | WO 03/099370 | 12/2003 |
| WO | WO 2004/008974 | 1/2004 |
| WO | WO 2004/014239 | 2/2004 |
| WO | WO 2004/069059 | 2/2004 |
| WO | WO 2004/069538 | 8/2004 |
| WO | WO 2004/073529 | 9/2004 |
| WO | WO-2005/065556 A1 | 7/2005 |
| WO | WO-2006/058042 A2 | 6/2006 |
| WO | WO-2006/069123 A1 | 6/2006 |
| WO | WO 2007/121405 | 10/2007 |
| WO | WO 2008/112435 | 9/2008 |
| WO | WO-2008/112436 A2 | 9/2008 |
| WO | WO-2008/127328 A1 | 10/2008 |
| WO | WO-2010/117883 A1 | 10/2010 |
| WO | WO-2010/123821 A1 | 10/2010 |
| WO | WO-2010/134914 A1 | 11/2010 |
| WO | WO-2011/030820 A1 | 3/2011 |

OTHER PUBLICATIONS

US 6,056,761, 05/2000, Gia et al. (withdrawn).
U.S. Appl. No. 12/297,419, filed Apr. 16, 2007, Strauss, et al.
U.S. Appl. No. 12/038,730, filed Feb. 27, 2008, Strauss et al.
International Search Report dated Sep. 10, 2008.
International Search Report dated Sep. 26, 2008.
Office Action (including English Translation) for Chinese Patent Application No. 200780018622.5 dated Aug. 2, 2010 in 8 total pages.
Copending U.S. Appl. No. 12/981,286, filed Dec. 29, 2010 (010C1).
Copending U.S. Appl. No. 13/010,671, filed Jan. 20, 2011 (012C1).
U.S. Appl. No. 13/308,476, filed Nov. 30, 2011.
U.S. Appl. No. 13/685,754, filed Nov. 27, 2012.
U.S. Appl. No. 13/841,836, filed Mar. 15, 2013.

* cited by examiner

IMPLANT, A MANDREL, AND A METHOD OF FORMING AN IMPLANT

RELATED APPLICATIONS

This application claims the benefit under 35 U.S.C. §119 (e) of provisional application Ser. Nos. 60/894,589 filed Mar. 13, 2007, 60/894,865 and 60/894,858 both filed on Mar. 14, 2007, all of which are hereby incorporated by reference in their entirety.

FIELD OF THE INVENTION

This invention relates to the forming of implantable coils and to coils formed by such methods as well as to a mandrel used to form the shape of a coil implant, a method of forming a coil implant, and a coil implant formed by such method or with such mandrel.

BACKGROUND OF THE INVENTION

Implants are delivered to a vascular site, such as an aneurysm, of a patient via a microcatheter to occlude or embolize the vascular site. Typically, the implant is engaged at the distal end of either the delivery microcatheter or the guidewire contained within the microcatheter and controllably released therefrom into the vascular site to be treated. The clinician delivering the implant must navigate the microcatheter or guide catheter through the vasculature and, in the case of intracranial aneurysms, navigation of the microcatheter is through tortuous microvasculature. This delivery may be visualized by fluoroscopy or another suitable means. Once the distal tip of the catheter or guidewire is placed in the desired vascular site, the clinician must then begin to articulate the implant in the vascular site to ensure that the implant will be positioned in a manner to sufficiently embolize the site. Once the implant is appropriately positioned, the clinician must then detach the implant from the catheter or guidewire without distorting the positioning of the implant. Detachment may occur through a variety of means, including, electrolytic detachment, chemical detachment, mechanical detachment, hydraulic detachment, and thermal detachment.

Previously, there had been provided 3-dimensional coils which are formed from a straight wire by detachment from the catheter or guidewire. The 3-dimensional coil is typically formed from a metal which upon detachment (e.g., in vivo) reconfigures from the straight wire into a coil shape or confirmation having a secondary structure (i.e., an extended or helically coil confirmation) which under ideal circumstances will comport to the shape of the vascular site to be embolized. However, the in vivo formed coils of the prior art invariably failed to provide shapes which comport to the vascular site and this results in the ineffective embolization of the vascular site. Even when the 3-dimensional coils of the prior art initially comport to the vascular site, the secondary structure of the resulting coils may not be sufficiently stable to retain their comportment with the vascular site. For example, 3-dimensional in vivo formed spherical coils tend to fold upon themselves which leads to secondary structure different from that of the vascular site. Likewise, 3-dimensional in vivo formed cubic coils often collapse on themselves, similar to a "stack of coins" rather than retaining their cubic shape.

In light of the above, there exists a need for a coil implant which substantially conforms to the vascular site to be embolized.

SUMMARY OF THE INVENTION

The invention, in one embodiment, is directed to an implant comprising a 3-dimensional coil designed to optimize packing into a vascular site, such as an aneurysm. It is contemplated that the implant of the invention, due to its secondary shape, is able to substantially conform to a vascular site thereby providing a more effective embolization. In particular, the shape of the 3-dimensional coil of this invention is composed of one or more unclosed mobius loops.

In one embodiment, this invention provides a 3-dimensional vascular coil comprising one or more unclosed mobius loops. The coil is biased to form a pattern corresponding to the winding pattern around a mandrel when released from the catheter or guidewire. The bias disposes the coil into a 3-dimensional shape that conforms with the exterior of a sphere. The winding pattern has at least one unclosed mobius loop distributed over the shape. In other embodiments, the winding pattern has at least two or three unclosed mobius loops distributed over the shape.

The shape of the coil can also conform with a pattern of eight substantially triangular shapes distributed over the surface of a sphere. In one embodiment, the eight substantially triangular shapes include four substantially triangular shapes with sides that bow outwards (convex) away from the center of the respective triangular shape, and four substantially triangular shapes with sides that bow inwards (concave) towards the center of the respective triangular shape. The shape of the coil can also have loops that conform with a path between the substantially triangular shapes, with a path that curves around the center of the sphere while also curving around at least four points corresponding to the triangular shapes, or with a path that can be described as generally following the contour of a hyperbolic parabloid or the contour of a saddle. Depending on the length of the coil, at least one and preferably multiple wraps of the coil will be made around the mandrel according to the winding pattern.

In one embodiment of the invention is provided a method of embolizing a vascular site of a patient comprising delivering the implant just described to the vascular site. The implant is delivered with a delivery device. The delivery device can be a microcatheter optionally including a guidewire and/or a positioner.

Another embodiment of the invention is directed to a mandrel. The mandrel includes a sphere and a plurality of markers, such as four markers, disposed on the exterior surface of the sphere. Optionally, one of the markers includes a stem. Each of the four markers define a pathway between adjacent markers, and the pathway preferably defines a winding pattern for a coil that is to be wrapped around the outer surface of the sphere. The winding pattern includes a series of sequential turns across the surface of the sphere corresponding to points where the pathway is disposed adjacent to a marker. The winding pattern also includes a series of sequential crossing points that correspond to midpoints between adjacent markers on the surface of the sphere.

In another embodiment of the invention is provided a method of forming the implant of the invention. The method of forming the coil includes the process of wrapping the coil over the mandrel according to the winding pattern. The method further includes subjecting the mandrel and wrapped coil to heat. The method also includes additional processing steps that form a finished coil from the wrapped coil.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications and patent applications cited herein are incorporated herein by reference in their entirety. Nothing herein is to be construed as an admission that the invention is not entitled to antedate such disclosure by virtue of prior invention.

It must be noted that as used herein and in the appended claims, the singular forms "a," "an," and "the" include plural references unless the context clearly dictates otherwise.

Methods of Embolizing a Vascular Site

The implant of the invention may be used to embolize a vascular site. This is best illustrated in FIGS. 1A, 1B, 1C, and 1D, which are described below. It should be noted that this method of delivery is one contemplated embodiment and that the implant of the invention may be delivered by a variety of other methods known by one of skill in the art.

Figure 1A:
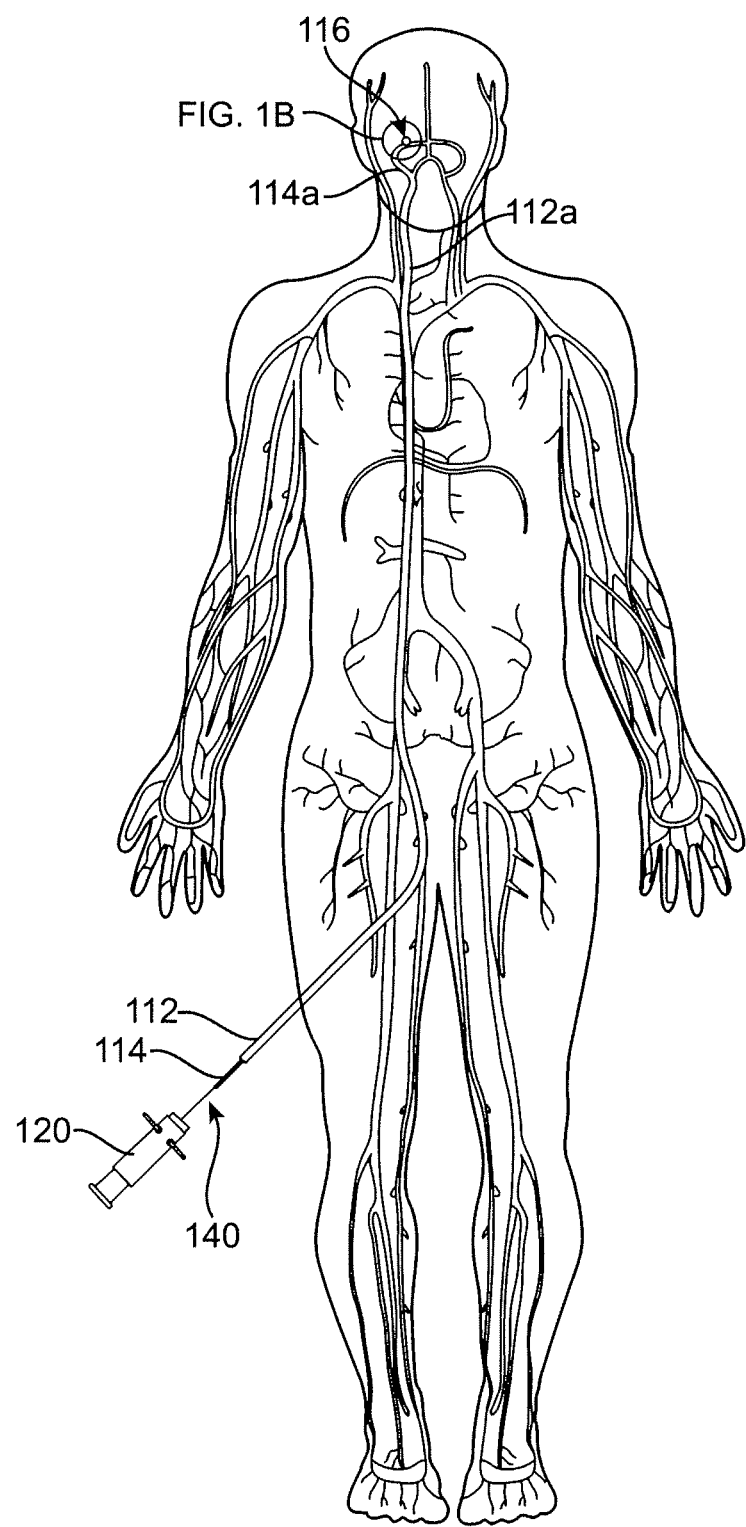
FIG. 1A is a plan view of a positioning system used to deliver a coil of the invention.
Figure 1B:
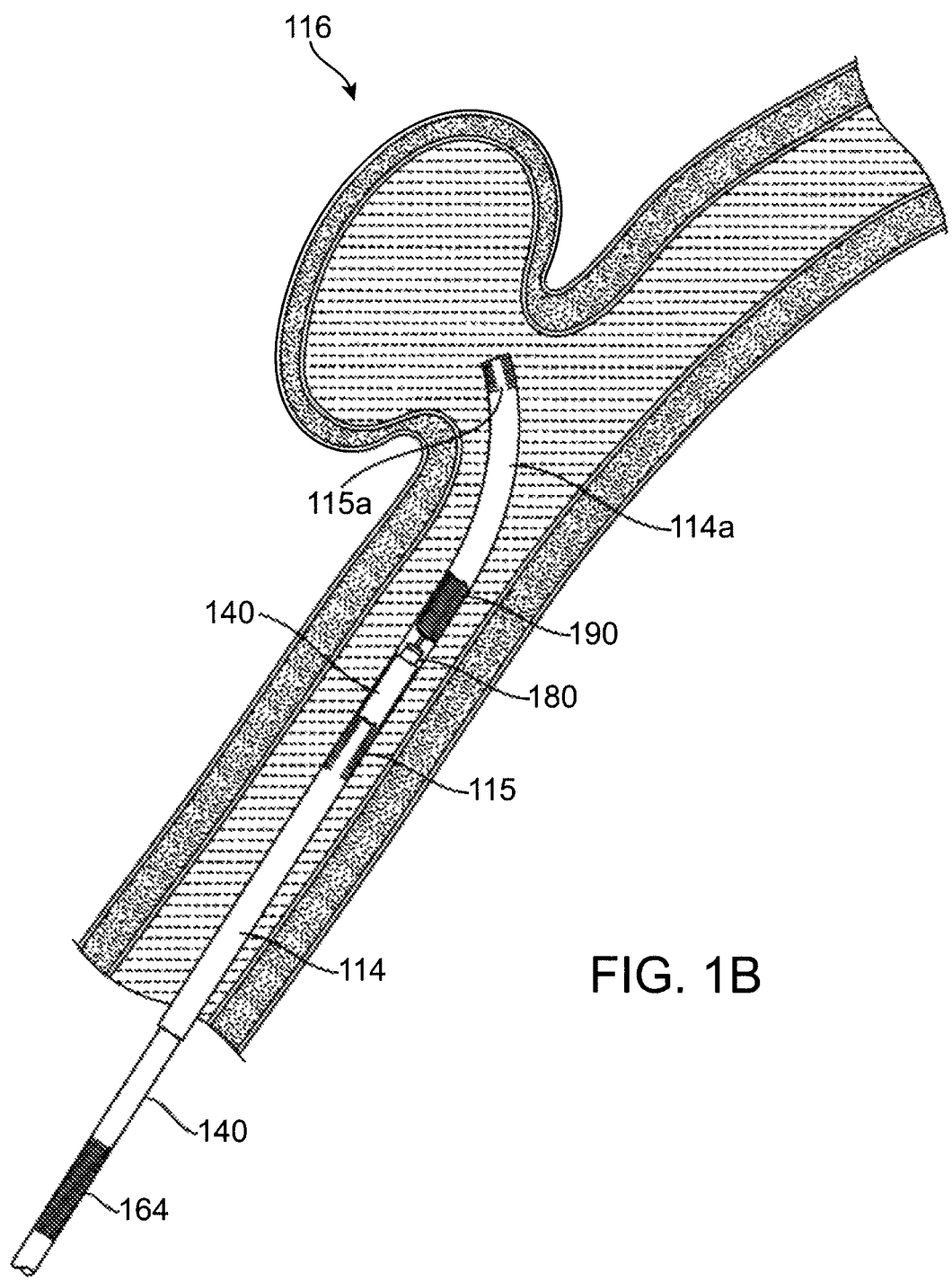
FIG. 1B is a closer view of a portion of FIG. 1A showing the positioning system in partial cross-section and an exemplary coil in a position within the human body prior to deployment of the coil.
Figure 1C:
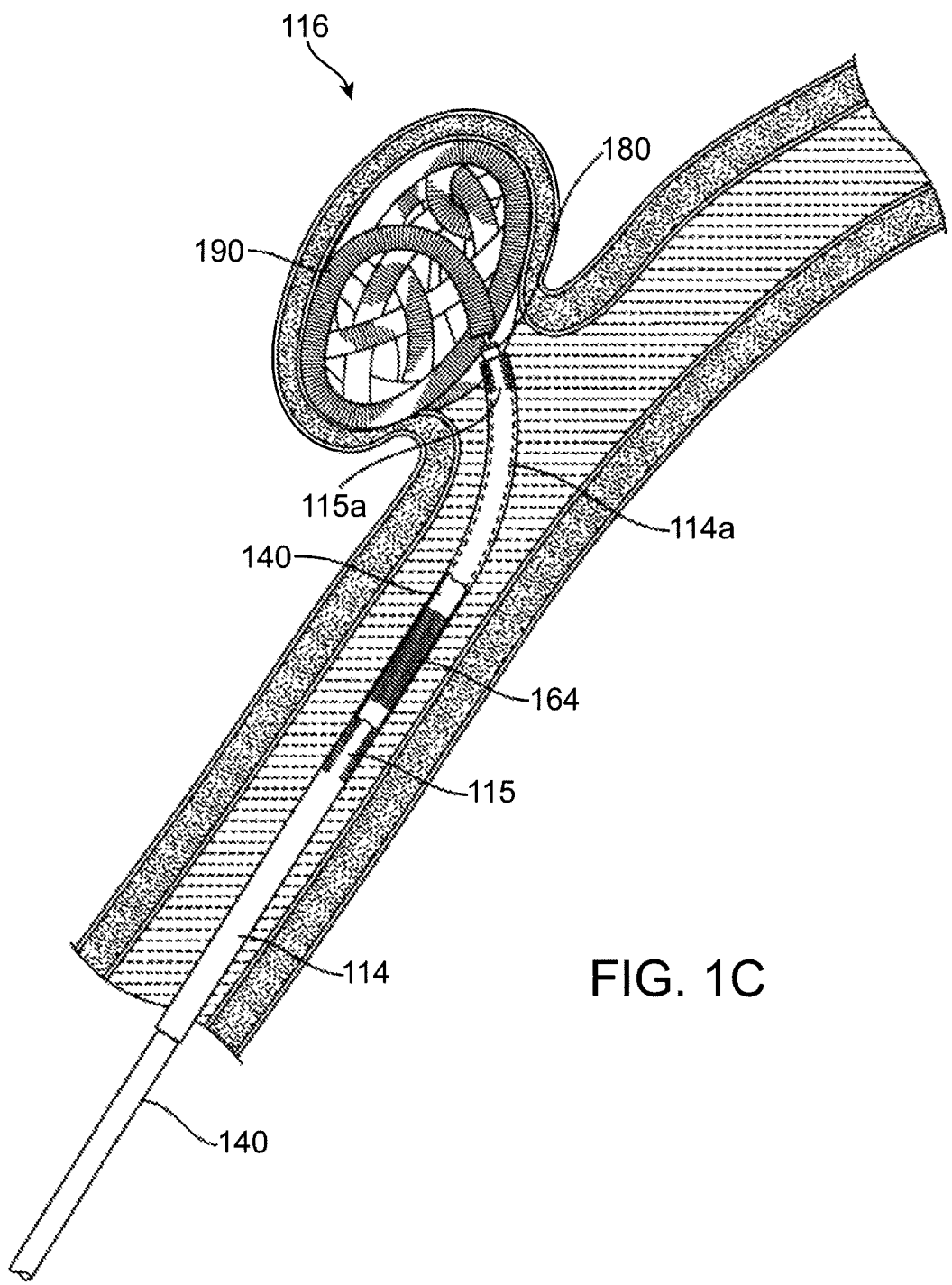
FIG. 1C is a closer view of a portion of FIG. 1A showing the positioning system in partial cross-section and an exemplary implant in another position within the human body after deployment but before detachment.

In the embodiment illustrated in FIG. 1A, an operator uses a guide catheter 112 to position a microcatheter 114 in a patient's vasculature. The procedure involves inserting the guide catheter 112 into the patient's vasculature through an access point such as the groin, and directing the distal end 112a of the guide catheter 112 through the vascular system until it reaches the carotid artery. After removing a guide wire (not shown) from the guide catheter 112, a microcatheter 114 is inserted into the guide catheter 112 and the distal end 114a of the microcatheter 114 subsequently exits the guide catheter distal end 112a and is positioned near the target site 116, such as an aneurysm in the patient's brain. As illustrated in FIGS. 1B and 1C, the microcatheter 114 includes microcatheter markers 115 and 115a that facilitate imaging of the distal end 114a of the microcatheter 114 with common imaging systems and, in the illustrated embodiment, the microcatheter markers 115 and 115a are made of a radiopaque material. After the distal end 114a reaches the target site 116, the positioning system (not shown) of the illustrated embodiment is then inserted into the microcatheter 114 to position the implant interface 180 at the distal end of the positioner 140 near the target site 116, as illustrated in FIG. 1C. If the implant 190 is being delivered in the procedure, the implant 190 is attached to the implant interface 180 prior to inserting the positioning system into the microcatheter 114. This mode of implant delivery is illustrated in FIGS. 1A, 1B, and 1C.

The delivery of the implant 190 is facilitated by disposing the microcatheter marker 115a near the target site 116, and aligning the microcatheter marker 115 with a positioner marker 164 in the positioner 140 which, when the two markers (markers 115 and 164) are aligned with each other as illustrated in FIG. 1C, indicates to the operator that the implant interface 180 is in the proper position for the release of the implant 190 from the positioning system (not shown). After depositing the implant 190 at the target site 116, a second implant 190 can be deposited at the target site 116 by removing the positioning system from the microcatheter 114 and inserting a second positioning system with an attached second implant 190 into the microcatheter 114 in a manner similar to the method used with the insertion of the first implant 190. The same procedure can be used for a third implant 190 and subsequent implants if clinically necessary. If the implant 190 is already in the patient's body to be retrieved or repositioned, the positioning system is inserted into the microcatheter 114 without the implant 190.

The Mandrel, the Implant, and the Method of Making the Implant

The invention, in one embodiment, is directed to an implant having a coil length that is biased to conform to a winding pattern, the winding pattern approximately conforming to a shape of an outer surface of a sphere. The winding pattern has at least one unclosed mobius loop (or a plurality of unclosed mobius loops) distributed over the shape. A mobius loop is formed by bringing the ends of that same coil around and twisting one end half of a turn before joining the ends. In this invention, the mobius loop is unclosed meaning the ends are not joined. This is best illustrated in FIG. 7C. A mobius loop is a strip having a single surface and is chiral.

Figure 3:
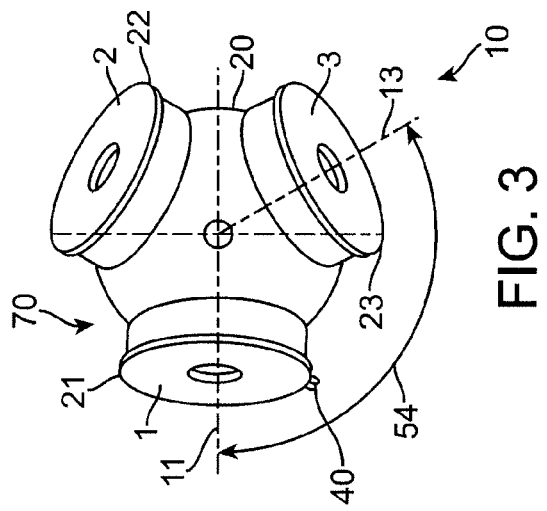
FIG. 3 is a top view of the mandrel of FIG. 2.
Figure 2:
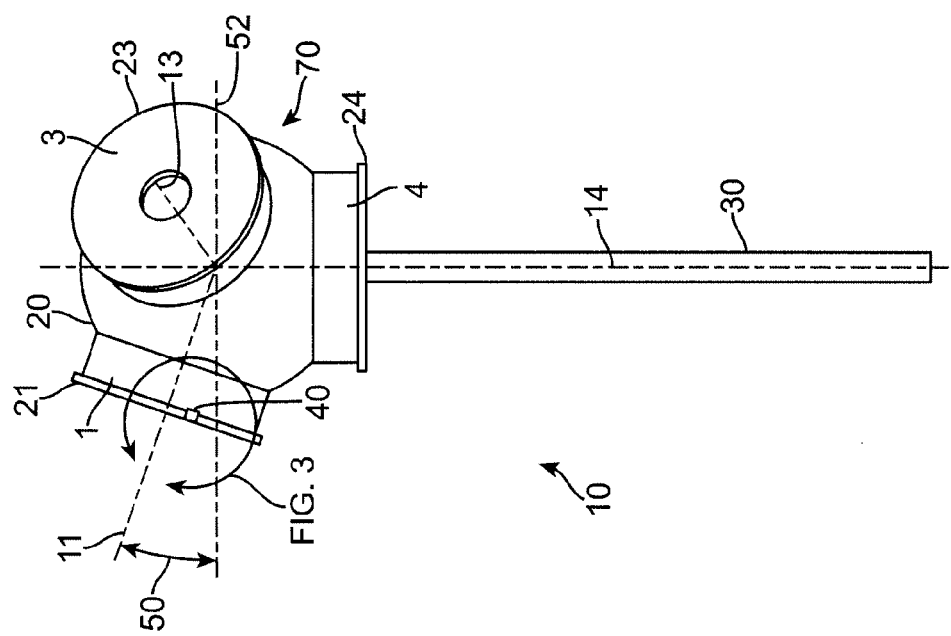
FIG. 2 is a plan view of a mandrel.
Figure 5:
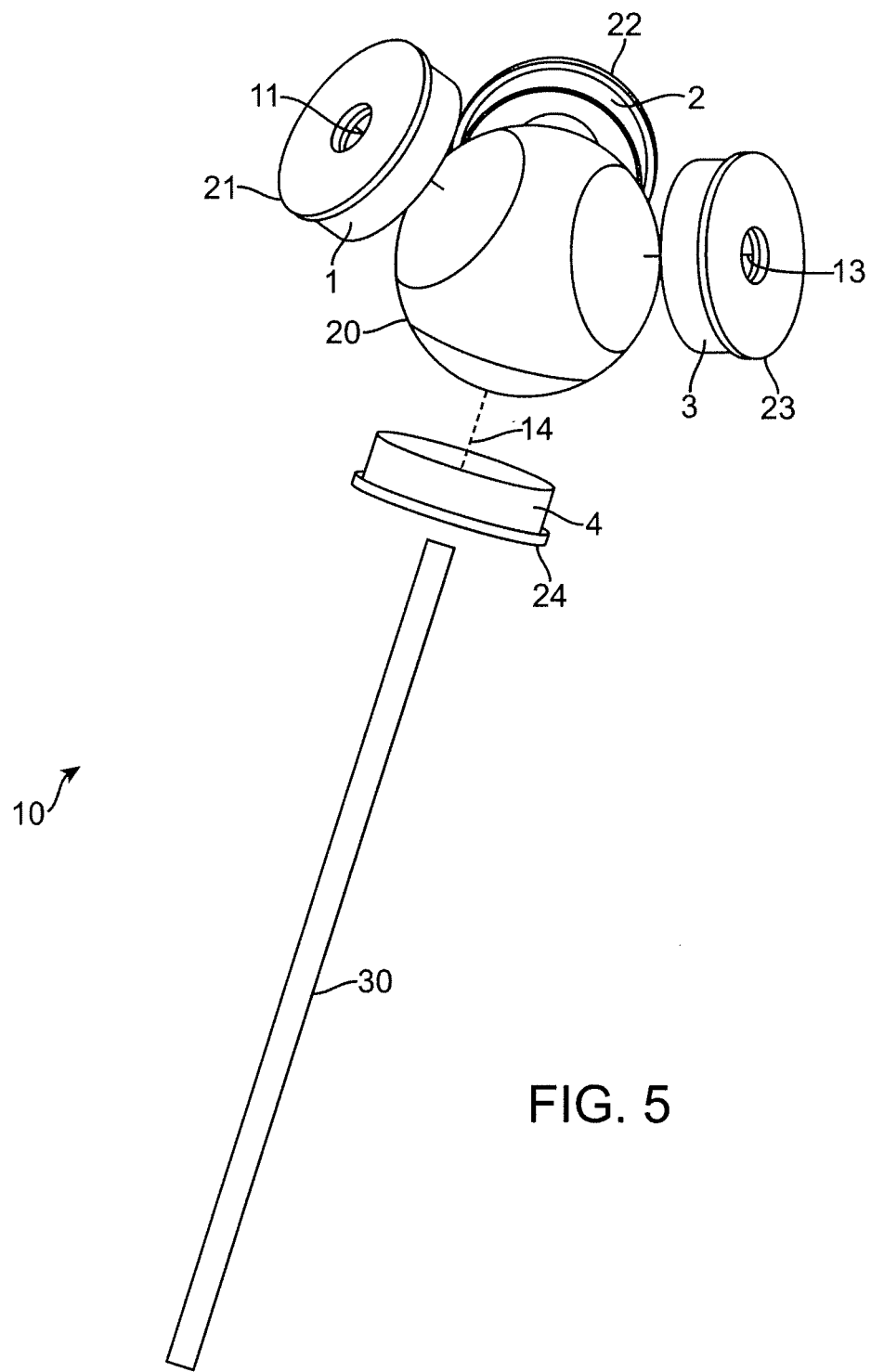
FIG. 5 is an isometric exploded view of the mandrel of FIG. 2.

To achieve the mobius loop, a mandrel is employed. The mandrel 10 illustrated in FIGS. 2 and 3 includes a sphere 20, four markers, and optionally a stem 30. The markers are mounted on the external surface of the sphere 20 at four locations. Each marker is designated with a numeric identifier of 1, 2, 3, or 4 as illustrated in FIGS. 2 and 3. Specifically, the stem 30 extends from marker 4. Marker 1 is on the left side of FIGS. 2 and 3 and is identifiable because it includes a starter tube 40. Marker 3 is to the right of marker 1 in FIG. 2 and to the bottom right in FIG. 3. Marker 2 is not viewable in FIG. 2 because it is on the rearward side of the figure, and is illustrated on the top right side in FIG. 3. FIG. 5 illustrates an isometric assembly view of the mandrel 10 without the starter tube 40.

The markers 1, 2, 3, and 4 are cylindrical and define longitudinal axes 11, 12 (not shown, but refers to the axis through marker 2), 13, and 14 for markers 1, 2, 3, and 4, respectively. Each axis 11, 12, 13, and 14 passes through the center of the sphere 20. The longitudinal axis 14 also passes through the center of the stem 30. The axes 11, 12, and 13 are at a vertical angle 50 to a plane 52 that is orthogonal to the axis 14, as illustrated in FIG. 2, which is about 19.5 degrees ±2.5 degrees. The axes 11, 12, and 13 are also at a horizontal angle 54 relative to each other, as illustrated in FIG. 3, which is about 120 degrees ±5 degrees.

On the radial extreme of each marker 1, 2, 3, and 4, relative to the center of the sphere 20, is optionally a cap 21, 22, 23, and 24. Each cap 21, 22, 23, and 24 has an outer diameter that is greater than the outer diameter of the corresponding marker 1, 2, 3, and 4. The outer diameter dimensions of the markers and caps and the outer diameter of the sphere 20 preferably vary according to the size of the mandrel 10. The size of the mandrel 10 corresponds to the size of the coil 60 that is to be formed with the mandrel 10.

The markers 1, 2, 3, and 4 are disposed on the outer surface of the sphere 20, and each marker 1, 2, 3, and 4 has an outer diameter that is smaller than the outer diameter of the sphere 20, which provides a spacing 70 between each marker 1, 2, 3, and 4 upon the surface of the sphere 20. This spacing 70 between each marker 1, 2, 3, and 4 provides a pathway 72 (FIG. 6) across the surface of the sphere 20 between each marker 1, 2, 3, and 4. The pathway 72 defines the winding pattern 74 (FIGS. 7A and 7B) for a coil 60 that is to be wrapped around the external surface of the sphere 20 in the spacing 70 between each marker 1, 2, 3, and 4.

The diameter of the marker 1, 2, 3, and 4 is selected to provide a coil of a desired softness and strength. The softness of the coil determines the coil's ability to conform to the vascular site. The larger the diameter of the marker 1, 2, 3, and 4, the larger the loop, the softer the coil, and the better the coil is able to conform to the vascular site. In one embodiment of the invention, the ratio of the diameter of the marker 1, 2, 3, and 4 to the diameter of the sphere is from about 0.5 to about 0.75, or 0.55 to about 0.75, or about 0.61 to about 0.65, or about 0.63.

The winding pattern 74 is initiated at the starter tube 40 on marker 1 as shown in FIG. 5. In one embodiment, an end of the coil 60 to be wound is inserted through the starter tube 40 in order to fix the coil 60 relative to the start tube 40. The initial wrap of the coil 60 is made around the outer diameter surface of the marker 1 until achieving a single wrap. A single wrap refers to a wrap that is from 270 circumferential degrees to 360 circumferential degrees. After achieving a single wrap, the coil 60 is wrapped along the pathway 72 disposed along the surface of the sphere 20 in the spacing 70 between adjacent markers 1, 2, 3, and 4, and the pathway 72 is not disposed along the outer diameter surfaces of the markers after the initial wrap.

Figure 6:
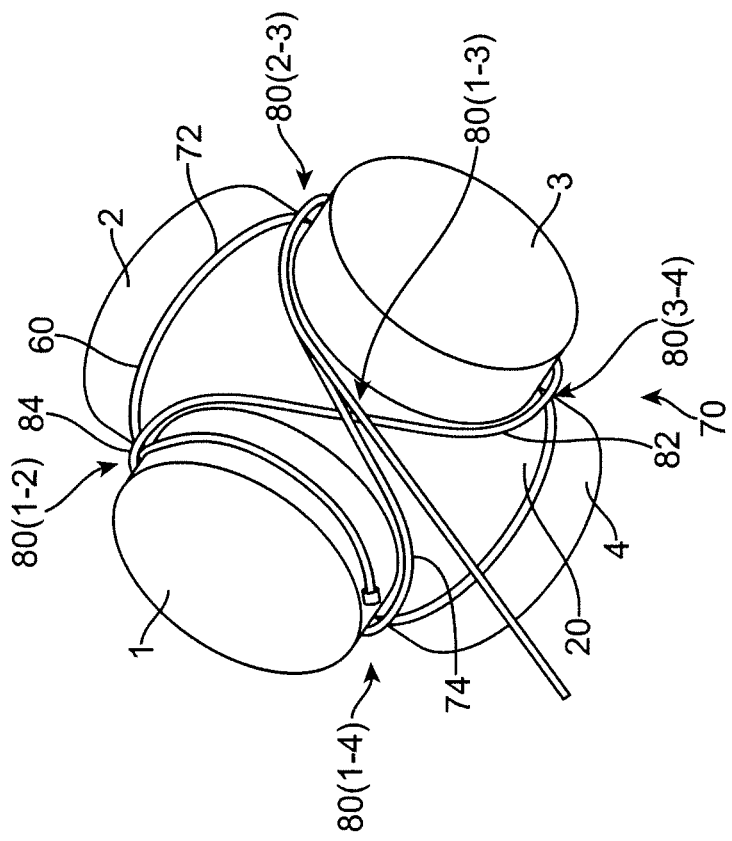
FIG. 6 is a schematic view of the winding pattern followed by a coil across the surface of the mandrel of FIG. 2, with a portion of the coil and the stem omitted.

The winding pattern 74 used for the wrapping of the coil 60 follows the pathway 72 on the external surface of the sphere 20. As illustrated in FIG. 6, the pathway 72 sequentially runs adjacent to each marker 1, 2, 3, and 4 until approaching a midpoint 80 on the surface of the sphere between adjacent markers. As illustrated in FIG. 6, the midpoint 1-3 is disposed at the midpoint 80 between markers 1 and 3 (80 (1-3)). Similar midpoints 80 are located on the sphere between each marker, with a total of six midpoints designated as follows: 1-2 (between markers 1 and 2), 1-3 (between markers 1 and 3), 1-4 (between markers 1 and 4), 2-3 (between markers 2 and 3), 2-4 (between markers 2 and 4), and 3-4 (between markers 3 and 4). When the pathway 72 approaches each midpoint 80, the pathway 72 moves away from a position adjacent to one marker and towards a position adjacent to a different marker. As illustrated in FIG. 6, the pathway 72 travels from a first position 82 adjacent to marker 3 to the midpoint 1-3 and then to a second position 84 adjacent to marker 2.

Figure 7A:
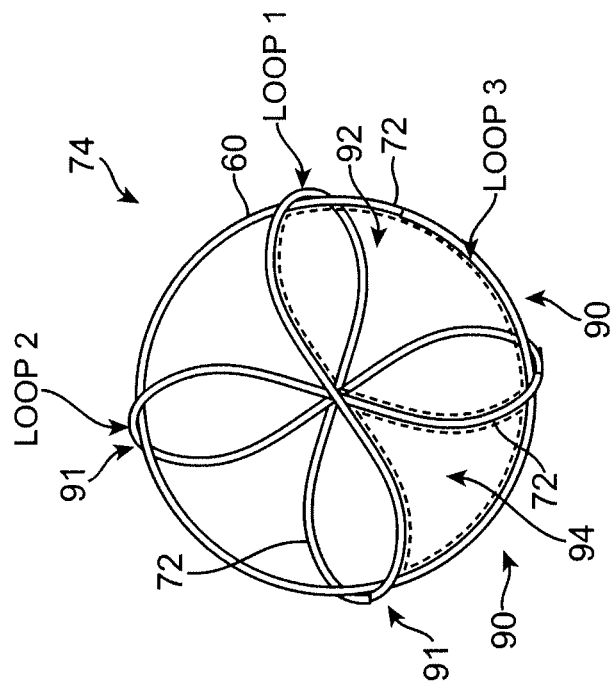
FIG. 7A is the schematic view of FIG. 6 with the mandrel omitted.
Figure 7B:
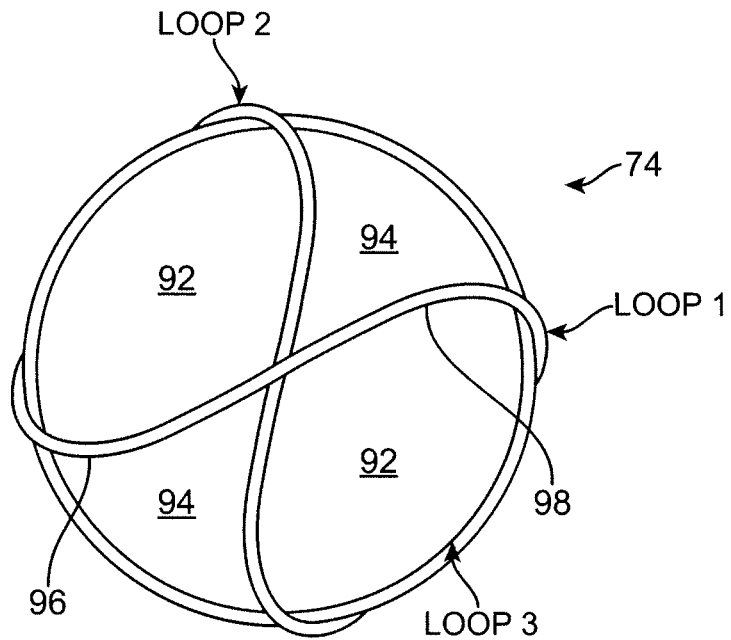
FIG. 7B shows the schematic of FIG. 7A with the rearward portion of the winding pattern omitted.
Figure 7C:
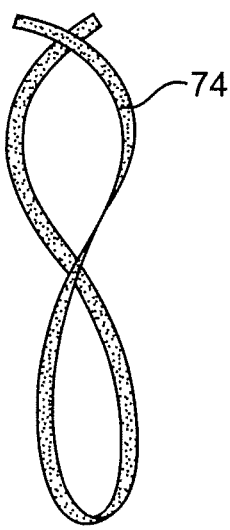
FIG. 7C shows a perspective of an unclosed mobius loop.

As can be appreciated from FIGS. 6 and 7A and 7B, the winding pattern 74 follows a pathway 72 that traces a pattern of substantially triangular shapes 90 over the surface of the sphere 20, with each apex 91 of each triangular shape 90 disposed at a midpoint 80. As can be further appreciated, two types of substantially triangular shapes 90 are apparent. One type of substantially triangular shape encloses each marker 1, 2, 3, and 4 and has sides that bow out away from the axes 11, 12, 13, and 14 of the markers. The other type of substantially triangular shape is disposed between the markers 1, 2, 3, and 4 and has sides that correspondingly bow in towards the center of the triangular shape and away from the axes of the markers. As illustrated in FIG. 7A with dashed lines, a total of four outwardly-bowed triangular shapes 92 and a total of four inwardly-bowed triangular shapes 94 are formed, which altogether follow the shape of the outer surface of the sphere 20.

It should be noted that the term "substantially triangular shape" refers to a 3-sided shape wherein the lines defining any or all of the sides are straight, concave or convex. In addition, when the substantially triangular shape is placed on the surface of a sphere, it is understood that the shape so formed will not be 2-dimensional but will otherwise comport to the 3-dimensional surface configuration of the underlying sphere.

Figure 8:
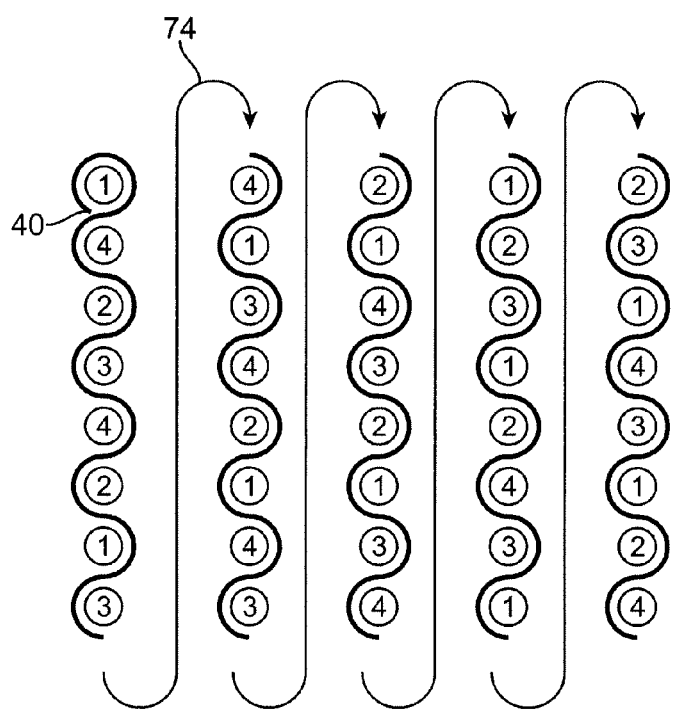
FIG. 8 is a representation of the winding pattern of FIG. 6.

FIG. 8 representatively illustrates the winding pattern 74 in regard to the markers 1, 2, 3, and 4 that are passed by the pathway 72. As indicates at the top left corner of FIG. 7A the winding pattern 74 is initiated at marker 1 at the starter tube 40, which is represented by a circle with a number 1, and the initial wind is shown wrapping around marker 1. Subsequent to the initial wind around marker 1, the winding pattern 74 travels to a position adjacent to marker 4, and then to a position adjacent to marker 2, and so on as illustrated. The winding pattern 74 subsequently repeats until the entire coil 60 is wrapped around the mandrel 10. The length of the wrap is dependent on the size of the coil.

The winding pattern 74 can also be represented by reference to the midpoints 80 that are sequentially traversed after the initial wind around marker 1. An initial portion of the winding pattern represented by FIG. 8 can thus be represented by the following pattern of midpoints traversed by winding pattern 74 after the initial wrap around marker 1: 1-4, 2-4, 2-3, 3-4, 2-4, 1-2, 1-3, 3-4, and so on.

Figure 9:
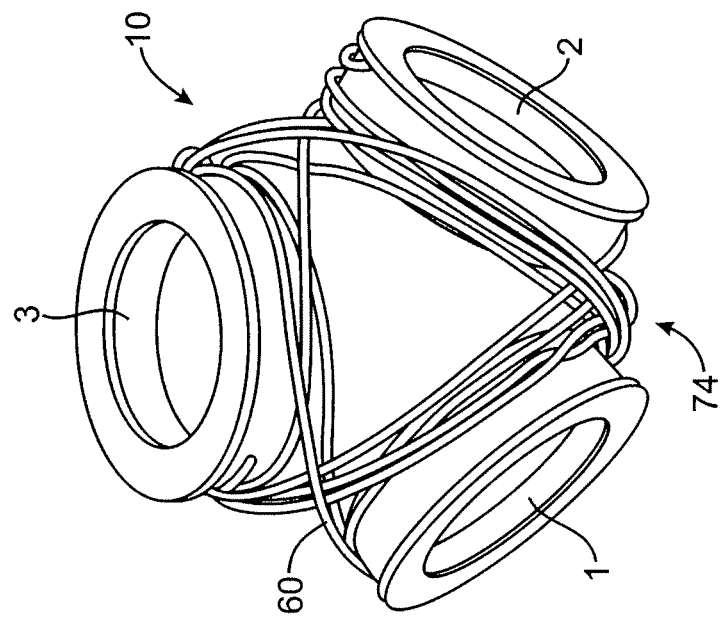
FIG. 9 and FIG. 10 are plan views of the mandrel of FIG. 2 showing the winding pattern of the coil around the mandrel.
Figure 10:
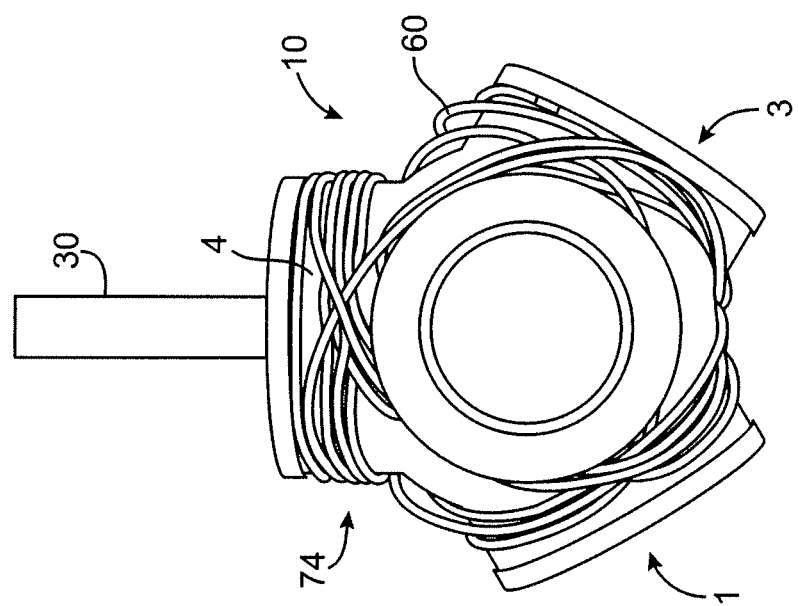

When forming the coil 60, the coil is wrapped around the mandrel 10 according to the winding pattern 74, with the beginning of the coil 60 disposed at the starter tube 40 (not shown). When the end the coil 60 is reached in the wrapping process, a portion of the coil 60 is sometimes not wrapped around the sphere 20 and is instead wrapped around the stem 30 (not shown) and stretched to secure the end of the coil in place. FIGS. 9 and 10 show the mandrel 10 and the wrapped coil 60. The wrapped coil 60 is subsequently subjected to a heat treatment process, similar to processes known in the art, that causes the coil 60 to thereafter have a bias to the winding pattern 74 of the mandrel 20, i.e., to have the predisposition to coil in a pattern similar to the winding pattern 74 of the mandrel 20. After the coil 60 has been subjected to the heat treatment process, the coil is removed from the mandrel 20 and further processed. This further processing preferably includes modification described in the next section. Additionally, the coil 60 may comprise a primary structure that is helical.

A coil 60 formed with the mandrel 10, applying the winding pattern 74, and the heat treatment process will have the loop pattern illustrated in FIGS. 7A and B. Preferably, the coil 60 will be biased to form a shape corresponding to the winding pattern 74, with a pattern of eight substantially triangular shapes evenly distributed and spherically curved so as to approximately form the outer diameter shape of the sphere 20, as schematically represented in FIG. 7A. The pattern of the coil 60 will also preferably form a series of four outwardly-bowed substantially triangular shapes corresponding to shapes 92 and a total of four inwardly-bowed substantially triangular shapes corresponding to shapes 94. Depending on the length of the coil 60, at least one and preferably multiple wraps of the coil will be made around the mandrel 10 according to the winding pattern 74, as illustrated in FIGS. 9 and 10.

As illustrated in FIG. 7B, which shows a forward-facing portion of the winding pattern 74 of FIG. 7A with the rearward-facing portion omitted for clarity, the winding pattern 74 includes three loops designated as loop 1, loop 2, and loop 3 that correspond with shapes 92 and 94. As can be appreciated from FIG. 7B, the loop 1, loop 2, and loop 3 portions of the winding pattern 74 follows a path that is disposed between adjacent shapes 92 and 94 that alternate position along the path of loop 1. In the path of loop 1, at point 96, the loop 1 is between a shape 92 on one side and a shape 94 on the other side. Farther along the path of loop 1, at point 98, the relative positions of shapes 92 and 94 to loop 1 have alternated so that loop 1 is between a shape 94 on one side and a shape 92 on the other side. As can also be appreciated from FIGS. 6 and 10, the same alternations of shapes 92 and 94 occur on the rearward-facing portion of the winding pattern 74, and the same alternations of shapes 92 and 94 occur with the loop 2 and loop 3 portions of the winding pattern 74. Yet another thing that can be appreciated from FIGS. 6 and 7A-B, is that the loops 1, 2, and 3 of winding pattern 74 follow paths that curve around the center of the sphere 20 while also curving around at least four points corresponding to shapes 92 and 94, which can be described as generally following the contour of a hyperbolic parabloid or the contour of a saddle. This is shown in FIG. 7B.

Materials

In one embodiment, the coil 60 may be made from a biocompatible metal that does not react adversely with the tissues and fluids when used in the body. The wire may be round, square, oval, triangular, or another shape. In certain embodiments the wire commonly has a diameter of from about 0.025 to about 0.09 mm, from about 0.03 to about 0.08 mm from about 0.04 to about 0.06 mm. In certain specific embodiments, the wire has a diameter of about 0.05 mm. In some embodiments the wire may be comprised only of a primary shape e.g., a simple single helix. In some embodiments the wire component may comprise a primary shape e.g., helical coil and a secondary shape.

In one embodiment, the material of the coil 60 is made of a material that may be heat set at a temperature of approximately 400° C. to about 700° C. In some embodiments, the coil is heat set at about 650° C. The metal or metal alloy can be radiopaque so that the position and location of the implant in the body can be monitored with radiological techniques. Suitable metals include, but are not limited to the noble metals such as the platinum group metals which include platinum, palladium, rhodium and rhenium as well as iridium, gold, silver, tungsten, and tantalum and alloys of these metals with one another. Additional metals include the super elastic metals such as "Nitinol" and the like. In one embodiment, the coil 60 is made of platinum alloy.

The mandrel of the invention may be made from a variety of materials, such as steel, so long as the material selected can withstand the heat set of the coil.

Modifications and Delivery of the Coil

As mentioned above, the coil of the invention may also undergo further processing, including being modified and used with an implant comprising other components. In one embodiment, the implant is modified to include a stretch-resistant member as described in "An Implant Including a Coil and a Stretch Resistant Member," U.S. Ser. No. 12/038,330, filed Feb. 27, 2008, which is hereby incorporated by reference.

In another embodiment, the coil is coupled with a delivery device. Any delivery device suitable for delivering a coil to a vascular site may be employed. Suitable microcatheters are described in WO 2007/121405 entitled "System and Method For Mechanically Positioning Intravascular Implants" which is hereby incorporated by reference in its entirety.

Figure 1D:
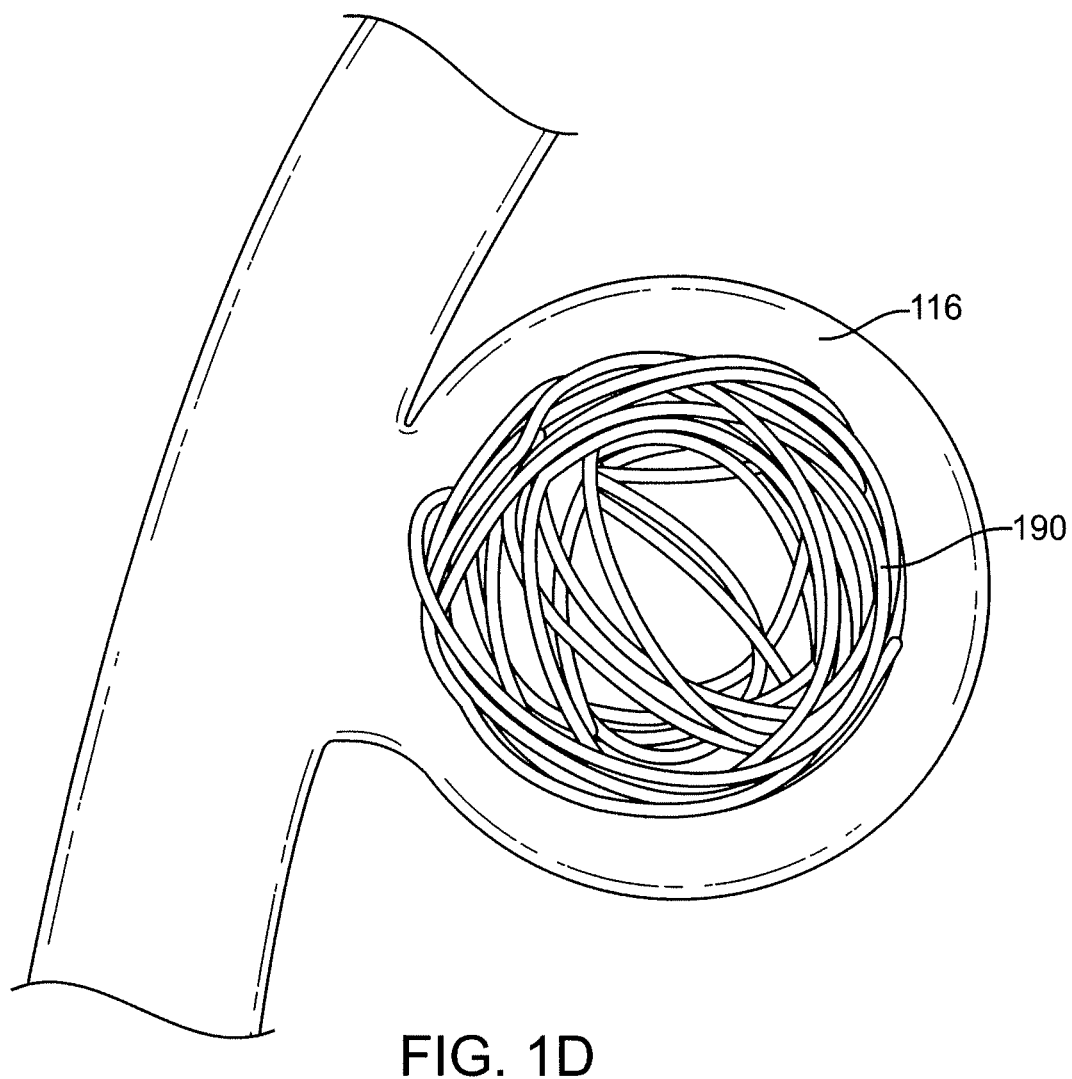
FIG. 1D is a shows the layup of the coil in the vascular site.
Figure 4:
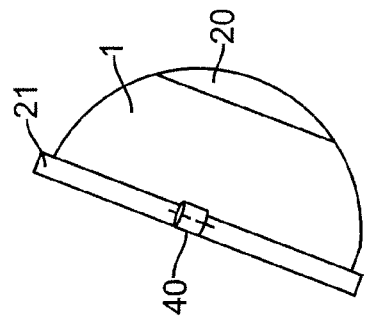
FIG. 4 is a close-up view of a portion of FIG. 2.

Regardless of the delivery device employed, after delivery of the implant to the vascular site, the implant substantially conform to the vascular site due to its three-dimensional shape. This is illustrated in FIG. 1D.

EXAMPLES

Example 1

Method of Making the Implant

An implant of the invention may be made by the following procedure.
1. Under microscope insert the distal end of the wire or coil into the starter tube.
2. Wind coil around mandrel as described above and in FIG. 8.
3. Heat set the coil and the mandrel. The temperature is from about 550° C. to about 650° C.

Example 2

Comparison of Other Three-Dimensional Shapes

The coil of the invention was tested and compared with coils having a cubic three-dimensional (3-D) shape and a spherical (or spheroidal) 3-D shape. The clinicians assessed the ability of the coil to compact into the vascular site and the ability of the coil to conform to the shape of the vascular site.

Protocol

The coils of the invention were obtained according to Example 1. The mobius loop coils of the invention were made on a 10 millimeter (mm) sphere with four 8 mm markers. The coils having a cubic 3-D were made by winding wire around a mandrel having six markers (rather than the four to obtain the coils of the invention), one on each face of the cube. One marker was 5 mm and the other five markers were 8 mm. The sphere was 10 mm. The spherical coil were obtained by winding wire around a base mandrel with eight markers. The sphere was again 10 mm and the markers were about 5 mm.

Once the coils were wound according to the patterns above, the coils were heat set at the temperature provided below.

In swine, 10 millimeter aneurysms were created. A 10 millimeter×30 centimeter coil was placed into the aneurysm several times without detaching it and then removing it from the catheter and deploying the next coil. This is illustrated in FIG. 1D.

The clinicians, who tested these coils in a blinded format, then delivered the coil to the aneurysm and provided qualitative feedback regarding the coil. Independent observers then translated each comment into a +1 (good), 0 (neutral), −1 (bad) scale. Some coils were marked with a score higher due to the comments of the doctors. Three of the coils of the mobius loop coils, three of the spherical coils and one of the cubic coils were assessed. Some of the coils tested contained stretch-resistant members as indicated below. The results are presented in Table 1.

TABLE 1

| Design | Stretch Resistant Member | Heat Set Temp. (° C.) | Observer 1 | | | Observer 2 | | | Observer 3 | | | Avg. | St. Dev. |
|---|---|---|---|---|---|---|---|---|---|---|---|---|---|
| | | | 1 | 2 | 3 | 1 | 2 | 3 | 1 | 2 | 3 | | |
| Cubic | — | 670 | 0 | 0 | 1 | 1 | 0 | −1 | −1 | 1 | 0 | 0.11 | 0.78 |
| Cubic | Nitinol | 550 | 0 | 0 | 1 | 0 | 1 | 1 | 0 | 1 | 1 | 0.56 | 0.53 |
| Cubic | — | 550 | 1 | 1 | 1.5 | 0 | 1 | 0 | 1 | 1 | 1 | 0.83 | 0.50 |
| Cubic | Polypropylene | 650 | 1 | 0.5 | 1 | 1 | 1 | 0 | 1 | 1 | 0 | 0.72 | 0.44 |
| Mobius Loop | — | 650 | 0 | 1 | 1 | 1 | −1 | 1 | 1 | 1 | | 0.63 | 0.74 |
| Mobius Loop | — | 650 | 1 | 1 | 0.5 | | | 1 | 0 | 1 | 1 | 0.79 | 0.39 |
| Mobius Loop | — | 550 | 1 | 1 | 1.5 | 1 | 0 | 1 | 1 | 1 | 1 | 0.94 | 0.39 |
| Spherical | Nitinol | 550 | −1 | −1 | 0 | −1 | −1 | 0 | −1 | −1 | 1 | −0.56 | 0.73 |
| Spherical | — | 550 | 0 | 0 | 0.5 | −1 | | | −1 | −1 | 1 | −0.21 | 0.81 |

The test was then repeated except the stretch resistant member was varied as indicated. Also, the score were evaluated on a score of 0 (bad) to 5 (good). The results are in Table 2 below.

TABLE 2

| Design | Stretch-Resistant Member | Overall Performance | Standard deviation |
|---|---|---|---|
| Cubic | Nitinol | 3.0 | 0.50 |
| Spherical | Nitinol | 3.25 | 0.29 |
| Cubic | Polypropylene | 3.67 | 0.29 |
| Mobius loop | Nitinol | 3.75 | 0.87 |
| Mobius loop | Polypropylene | 4.17 | 0.58 |

As can be seen in Table 1 and 2, the mobius loop coil is preferred for its overall performance and repeatability over the cubic and spherical coils.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

We claim:

1. An implant comprising:
a coil having a coil length that is biased to conform to a winding pattern, the coil comprising a primary, substantially linear configuration for delivery of the coil to a vascular site, and a secondary, substantially spherical configuration in an unrestrained state for positioning at said vascular site, the winding pattern approximately conforming to an outer surface of a sphere, the winding pattern consisting of only substantially triangular shapes, each triangular shape having a center, four of the triangular shapes having sides that bow outward away from the center, four of the triangular shapes having sides that bow inward towards the center, the coil comprising a proximal end, a distal end, and a longitudinal axis that, when the coil is in the linear configuration, extends from the proximal end to the distal end, the coil formed by winding about a mandrel and twisting the proximal end at least half a turn with respect to the distal end about the longitudinal axis.

2. The implant of claim 1, wherein the coil substantially conforms to a vascular site.

3. The implant of claim 1, wherein the coil is comprised of a metal wire.

4. The implant of claim 3, wherein the wire is comprised of a metal selected from the group consisting of platinum, palladium, rhodium, rhenium, iridium, gold, silver, tungsten, tantalum, an alloy of two or more of these metals, or a super elastic metal.

5. The implant of claim 4, wherein the wire is a platinum alloy.

6. A method of embolizing a vascular site of a patient comprising delivering an implant of claim 1 via a delivery device to the vascular site thereby embolizing the vascular site.

7. The method of claim 6, wherein the implant substantially conforms to the vascular site.

8. The method of claim 7 comprising delivering additional implants to the vascular site.

9. An implant comprising:
a coil having a coil length that is biased to conform to a winding pattern, the coil comprising a primary, substantially linear configuration for delivery of the coil to a vascular site, and a secondary, substantially spherical configuration in an unrestrained state for positioning at said vascular site, the winding pattern approximately conforming to an outer surface of a sphere, the winding pattern consisting of only substantially triangular shapes, each triangular shape having a center, four of the triangular shapes having sides that bow outward away from the center, four of the triangular shapes having sides that bow inward towards the center.

10. The implant of claim 9, wherein the coil substantially conforms to a vascular site.

11. The implant of claim 9, wherein the coil is comprised of a metal wire.

12. The implant of claim 11, wherein the wire is comprised of a metal selected from the group consisting of platinum, palladium, rhodium, rhenium, iridium, gold, silver, tungsten, tantalum, an alloy of two or more of these metals, or a super elastic metal.

13. The implant of claim 12 wherein the wire is a platinum alloy.

14. A method of embolizing a vascular site of a patient comprising delivering an implant of claim 9 via a delivery device to the vascular site thereby embolizing the vascular site.

15. The method of claim 14, wherein the implant substantially conforms to the vascular site.

16. The method of claim 15 comprising delivering additional implants to the vascular site.

* * * * *